(12) United States Patent
Satyamurthy et al.

(10) Patent No.: US 8,674,101 B2
(45) Date of Patent: Mar. 18, 2014

(54) NUCLEOPHILIC FLUORINATION OF AROMATIC COMPOUNDS

(75) Inventors: Nagichettiar Satyamurthy, Los Angeles, CA (US); Jorge R. Barrio, Agoura Hills, CA (US)

(73) Assignee: The Regents of the University of California, Oakland, CA (US)

( * ) Notice: Subject to any disclaimer, the term of this patent is extended or adjusted under 35 U.S.C. 154(b) by 308 days.

(21) Appl. No.: 13/054,458

(22) PCT Filed: Jul. 13, 2009

(86) PCT No.: PCT/US2009/004063
§ 371 (c)(1),
(2), (4) Date: Apr. 1, 2011

(87) PCT Pub. No.: WO2010/008522
PCT Pub. Date: Jan. 21, 2010

(65) Prior Publication Data
US 2011/0178302 A1    Jul. 21, 2011

Related U.S. Application Data

(60) Provisional application No. 61/080,524, filed on Jul. 14, 2008.

(51) Int. Cl.
*C07D 241/18*    (2006.01)
(52) U.S. Cl.
USPC ......................................................... 544/408

(58) Field of Classification Search
USPC .......................................................... 544/408
See application file for complete search history.

(56) References Cited

U.S. PATENT DOCUMENTS
2007/0092441 A1    4/2007   Wadsworth

FOREIGN PATENT DOCUMENTS
WO    WO2005/097713    10/2005

OTHER PUBLICATIONS
EPO Examination Report in corresponding EP Application No. 09788911.7 dated Jun. 12, 2012.

*Primary Examiner* — Brian McDowell
(74) *Attorney, Agent, or Firm* — Koppel, Patrick Heybl & Philpott; Michael J. Ram

(57) ABSTRACT

Iodylbenzene derivatives substituted with electron donating as well as electron withdrawing groups on the aromatic ring are used as precursors in aromatic nucleophilic substitution reactions. The iodyl group ($IO_2$) is regiospecifically substituted by nucleophilic fluoride to provide the corresponding fluoroaryl derivatives. No-carrier-added [F-18]fluoride ion derived from anhydrous [F-18](F/Kryptofix, [F-18]CsF or a quaternary ammonium fluoride (e.g., $Me_4NF$, $Et_4NF$, $n-Bu_4NF$, $(PhCH_2)_4NF$) exclusively substitutes the iodyl moiety in these derivatives and provides high specific activity F-18 labeled fluoroaryl analogs. Iodyl derivatives of a benzothiazole analog and 6-iodyl-L-dopa derivatives have been synthesized as precursors and have been used in the preparation of no-carrier-added [F-18]fluorobenzothiazole as well as 6-[F-18]fluoro-L-dopa.

9 Claims, 23 Drawing Sheets

Where

Ar = a　　　　b　　　　c　　　　d e　　　　f　　　　g　　　　h i　　　　j　　　　k　　　　l m　　　　n a=NaOCl or dimethyldioxirane
b=K$^{18}$F/Kryptofix, Cs$^{18}$F or quaternary ammonium[$^{18}$F]fluoride Where:
 a=BBr$_3$/CH$_2$Cl$_2$
 b=ClCH$_2$OCH$_3$/Et$_3$N
 c=Dimethyldioxirane
 d=KF/Kryptofix
 e=K$^{18}$F/Kryptofix
 f=57%HI
 g=37%HCl Where:
  a=C₂H₅OH/HCl
  b=(Boc)₂O/Et₂N/DMF
  c=I₂/PhI(OCOCF₃)₂
  d=(Boc)₂O/4-(dimethylamino)pyridine/THF
  e=Dimethyldioxirane Where:
a=BrCH₂OCH₃/CH₃COOH
b=(2R)-2,5-dihydro-3,6-methoxy-2-isopropylpyrazine/THF/n-BuLi
c=Dichloromethyl methyl ether/SnCl₄/CH₂Cl₂
d=Dimethyldioxirane
e=BCl₃ or BBr₃
f=(Boc)₂O Where:
a=(S)-(-)-1-Boc-2-tert-butyl-3-methyl-4-imidazolidinone
b=Dichloromethyl methyl ether/SnCl$_4$/CH$_2$Cl$_2$
c=Dimethyldioxirane Where:
a=K$^{18}$F/Kryptofix or quarternary ammonium [$^{18}$F]fluoride Where:
    a=K$^{18}$F/Kryptofix or quartenary ammonium [$^{18}$F]
    b=3-chloroperoxybenzoic acid
    c=H$^+$ Column: Phenomenex Gemini C-18 (250 x 4.6mm) ; 5μm
Eluent: CH$_3$OH : 25 mM NH$_4$OAc in water (70:30)
Flow rate: 2.0 mL/min
Detector: Radioactivity (gamma)

Column: Phenomenex Gemini C-18 (250 x 4.6mm; 5μ)

Eluent: CH₃OH : 25mM NH₄OAc in water (70:30)

Flow rate: 2.0 mL/min

Detector: Radioactivity (gamma)

Column: Waters μBondapak C-18 (300x3.9mm)

Eluent: 0.1% HOAc in water : CH₃OH (97:3)

Flow rate: 1.0mL/min

Detector: Radioactivity (gamma)

NUCLEOPHILIC FLUORINATION OF AROMATIC COMPOUNDS

This is a National Stage Application of PCT/US2009/004063, filed Jul. 13, 2009, published as WO 2010/008522 A2, and claiming priority of U.S. provisional No. 61/080,524 filed 14 Jul. 2008.

This application claims benefit of U.S. Provisional Application 61/080,524, filed Jul. 14, 2008.

This invention was made with Government support under Grant No. DE-FG02-06ER64249 awarded by the US Department of Energy. The federal government may have certain rights in the invention.

BACKGROUND

Incorporation of positron emitting fluorine-18 (half-life=110 min) into aromatic ring systems plays a very important role in the development of novel biomarkers for utilization in Positron Emission Tomography (PET). Two major pathways are commonly used for this process, namely electrophilic and nucleophilic fluorine substitution reactions. Electrophilic fluorination reactions can only provide products with low specific activities (ca 1-5 Ci/mmol) because of the unavoidable addition of non-radioactive elemental fluorine (often called carrier fluorine) during the current production techniques for F-18 labeled fluorine. The combination of labeled fluorine and carrier fluorine is referred to as $[^{18}F] F_2$. A typical example of electrophilic radiofluorination can be summarized by the following reaction:

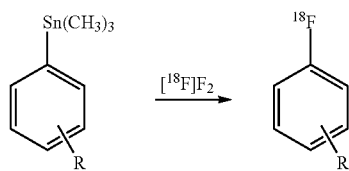

Where R=electron withdrawing groups (e.g. CHO, COOEt, CN, $NO_2$ etc) or electron donating groups (e.g. $CH_3$, $OCH_3$ etc)

Low specific activity biomarkers prepared by electrophilic aromatic radiofluorination reactions with [F-18]fluorine and reagents derived from it are generally useful for monitoring enzyme-mediated processes (e.g., aromatic amino acid decarboxylase dependent transformation). However, they are unsuitable for investigation of biochemical processes such as receptor systems or enzyme inhibition.

Nucleophilic fluorination of aromatic rings, on the other hand, provides products with high specific activity (ca 1,000-10,000 Ci/mmol). High specific activity [F-18]fluoride ion, the fluorinating agent for nucleophilic substitution reactions, is more conveniently prepared in large quantities (1-10 Ci) unlike molecular [F-18]fluorine which is obtained in 0.3-0.7 Ci levels. Facile displacement of certain leaving groups (e.g. nitro and quaternary ammonium moiety) in aromatic systems activated by electron withdrawing substituents (e.g. CHO, $COCH_3$, $NO_2$, CN, $COOCH_3$) by high specific activity [F-18] fluoride ion is well documented and can be depicted as follows:

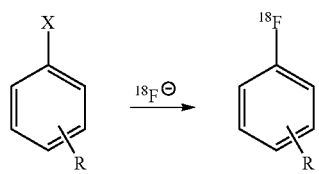

Where R=electron withdrawing groups (e.g. CHO, COOEt, CN, $NO_2$ etc) located at ortho or para position with respect to the group X, and X=$NO_2$ or $^\oplus N(CH_3)_3$ Simple deactivated aromatic rings such as the example cited above provide [F-18]fluorinated products in good radiochemical yields (30-80%). However, as the complexity of the aromatic ring system increases (which is the case with almost all the useful biomarkers) the radiochemical yields obtained by this reaction drops drastically. Further, aromatic compounds lacking electron withdrawing/deactivating substituents (i.e. CHO, CN, $NO_2$ etc) fail to undergo this reaction. Two different routes have been formulated for aromatic nucleophilic fluorination reactions for rings that carry no deactivating substituents (e.g. CHO, $NO_2$, CN etc) or carry groups that are electron donating in nature (e.g. $CH_3$, $OCH_3$). The following reactions have been identified for aromatic nucleophilic substitution reactions for phenyl rings that bear electron-donating groups:

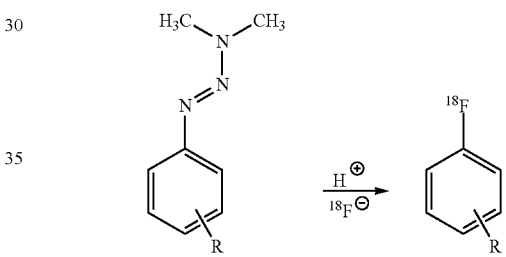

Where R=electron donating groups (e.g. $CH_3$, $OCH_3$ etc) located at ortho, meta and para positions with respect to the triazene group.

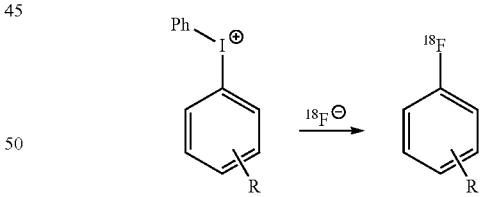

Where R=electron donating groups (e.g. $CH_3$, $OCH_3$ etc) located at ortho, meta and para positions with respect to the iodonium group.

The radiochemical yields obtained for the fluorinated products by the above two reactions are generally less then 60% with simple molecules and they generally both fail to be useful for certain complex systems.

Thus, there is a great need for fluorination reactions and particularly for nucleophilic aromatic fluorination reaction conditions that are suitable for the preparation of F-18 labeled biomarkers having a variety of substituents, including electron donating groups. Use of such reactions will make many different biomarkers easily accessible and will facilitate development and utilization of novel molecular imaging probes in PET. It is also anticipated that similar reactions with various nucleophiles would expand the utility of the approach to a multitude of labeled and unlabeled molecules.

SUMMARY

A novel aromatic nucleophilic radiohalogenation reaction which proceeds without the addition or inclusion of any stable/non-radioactive carrier ion is described. In particular, a radiofluorination reaction which proceeds without the addition or inclusion of a carrier ion for an [F-18] fluorination process is set forth. In a preferred procedure, this "no-carrier-added" [F-18] fluoride ion is reacted with an iodylbenzene derivative, with the fluoride ion nucleophilically substituting the iodyl group ($IO_2$) on the aromatic ring, resulting in regiospecific F-18 labeled aromatic compounds. The no-carrier-added [F-18] fluoride ion is produced by proton irradiation of [O-18] water using a cyclotron. The [F-18] fluoride ion is then treated with potassium carbonate and a Kryptofix® ligand and the aqueous solution is evaporated. The residue is further dried using azeotropic distillation with acetonitrile to provide a dried [F-18] fluoride ion in the Kryptofix® structure. Alternatively, no-carrier-added [F-18] CsF or [F-18] quaternary ammonium fluorides (e.g., $Me_4NF$, $Et_4NF$, n-$Bu_4NF$, $(PhCH_2)_4NF$) are used instead of [F-18] KF/Kryptofix. The iodyl compound dissolved in dry DMSO is then reacted with the dried [F-18]fluoride ion to form the no-carrier-added [F-18] fluoroaryl derivative which is isolated using chromatographic techniques. These [F-18] fluorinated aromatic compounds can have applications in Positron Emission Tomography (PET).

DETAILED DESCRIPTION

Figure 1:
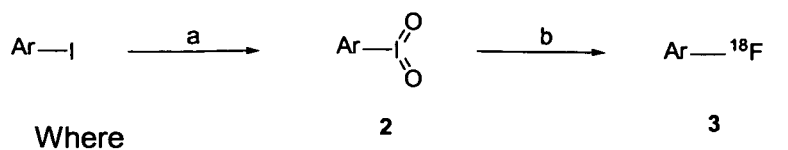
FIG. 1 shows the basic chemical reaction sequence for the preparation of the iodylbenzene derivatives and their subsequent reaction with [F-18] fluoride ion to produce the corresponding no-carrier-added [F-18] labeled aryl analogs.
Figure 1:
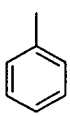
Figure 1:
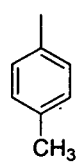
Figure 1:
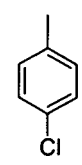
Figure 1:
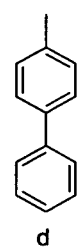
Figure 1:
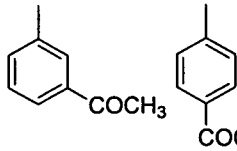
Figure 1:
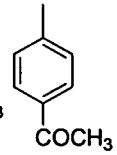
Figure 1:
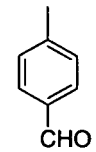
Figure 1:
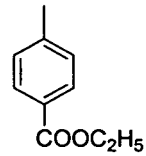
Figure 1:
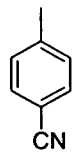
Figure 1:
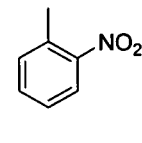
Figure 1:
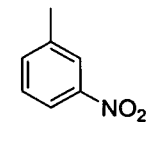
Figure 1:
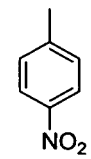
Figure 1:
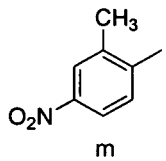
Figure 1:
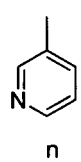

The basic reaction sequence described herein is shown in FIG. 1. Substituted iodobenzenes are oxidized by sodium hypochlorite (bleach) or dimethyldioxirane as reported in the literature (D. H. R. Barton, C. R. A. Godfrey, J. W. Morzycki, W. B. Motherwell and S. V. Ley, "A Practical Catalytic Method for the Preparation of Steroidal 1,4-dien-3-ones by Oxygen Atom Transfer from Iodoxybenzene to Diphenyl Diselenide." *J. Chem. Soc. Perkin Trans.* 1, pp 1947-1952 (1982); A. Y. Koposov, R. R. Karimov, I. M. Geraskin, V. N. Nemykin and V. V. Zhdankin, "2-Iodylphenol Ethers: Preparation, X-ray Crystal Structure, and Reactivity of New Hypervalent Iodine (V) Oxidizing Reagents." *J. Org. Chem.*, 71, pp 8452-8458 (2006)) to provide the corresponding iodylbenzene derivatives.

In one embodiment, the iodyl precursors 2a-n were synthesized as follows: Glacial acetic acid (5.0 mL) was added to a vigorously stirring mixture of an iodobenzene derivative 1a-n (2.0 g) and NaOCl (bleach, 25 mL) at room temperature. The reaction mixture was then stirred for 12 h and filtered. The solid material was washed with water followed by acetone. The solid material was recrystallized from water to obtain pure iodyl derivatives.

In a second embodiment, the same iodyl precursors 2a-n were prepared by a different reaction. In this case, a fresh solution of dimethyldioxirane (DMDO) was first prepared as set forth in R. W. Murray and M. Singh, "Synthesis of Epoxides using Dimethyldioxirane: trans-Stilbene Oxide." *Org. Syn. Coll. Vol.* 9., pp 91-96 (1998). Forty milliliters of acetone were added to a solution of sodium bicarbonate (12.0 g) in water (50 mL). The white suspension formed was cooled in an ice bath at 0° C. and solid Oxone® (Oxone® is potassium peroxymonosulfate, $KHSO_5$, sold by DuPont Company) was added over a period of 10-15 min with vigorous stirring. The mixture was stirred at 0° C. for an additional period of 5 min and then distilled at room temperature for 45-60 min under vacuum (100 ton). A pale yellow distillate of DMDO (~30 mL) in acetone, collected in a flask cooled in a −78° C. bath, was dried with anhydrous sodium sulfate and filtered. The pale yellow filtrate containing DMDO was used immediately in the next step.

A solution of the iodobenzene derivative 1a-n (0.2 g) in anhydrous dichloromethane (5.0 mL) was cooled in an ice bath and a freshly prepared solution of DMDO in acetone (30 mL) was added dropwise. The reaction mixture was stirred at 0° C. for a further period of 3 h followed by at room temperature overnight. The reaction mixture was filtered and the solid material was washed with acetone and recrystallized from water to yield pure iodyl derivatives 2a-n in 60-80% yield.

The iodylbenzene derivatives 2a-n, thus synthesized by the two methods described above, were characterized by one and two dimensional $^1$H NMR, $^{13}$C NMR, $^{15}$N NMR (where appropriate) and electrospray ionization (ESI) mass spectroscopy and the data are provided below in Examples 1-14. Representative two dimensional NMR spectra are given in FIGS. 5, 6 and 7.

Figure 2:
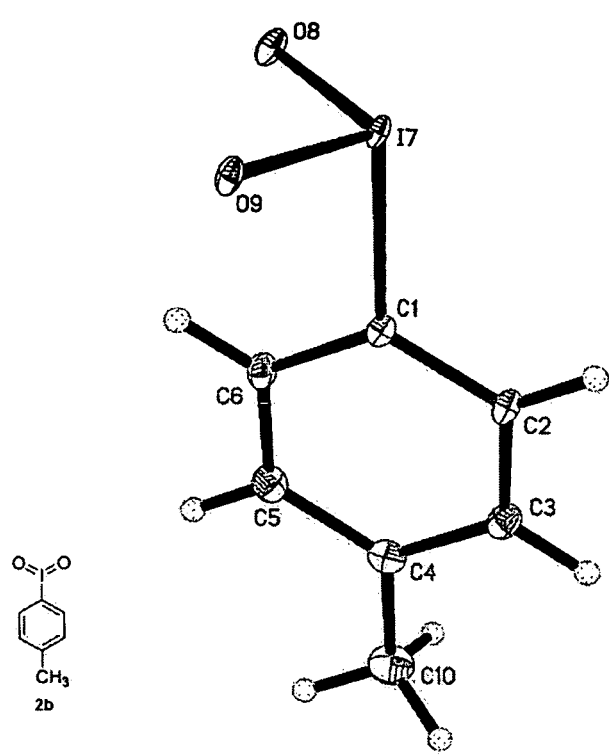
FIG. 2 shows 4-methyliodylbenzene (2b) and the single crystal X-ray structure for that compound.
Figure 3:
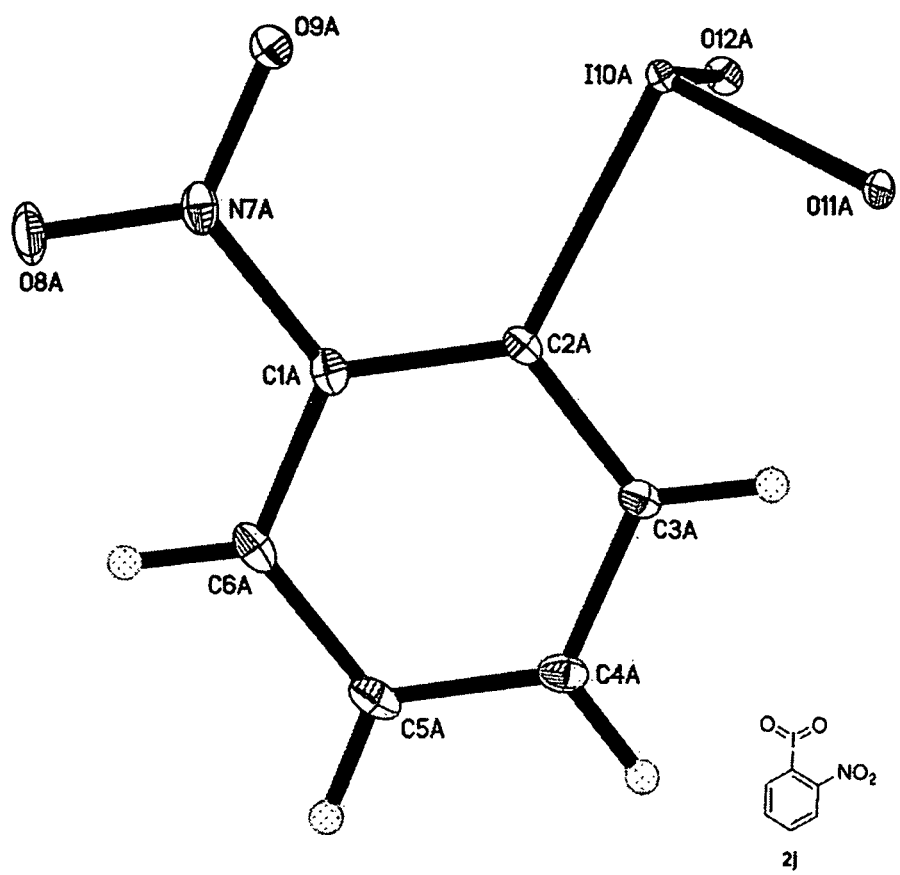
FIG. 3 shows 2-nitroiodylbenzene (2j) and the single crystal X-ray structure for that compound.
Figure 4:
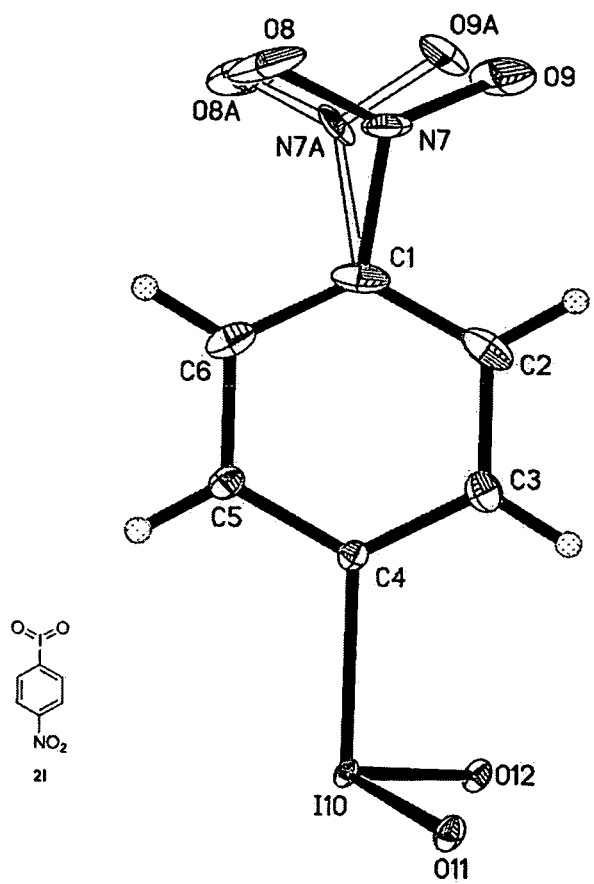
FIG. 4 shows 4-nitroiodylbenzene (2l) and the single crystal X-ray structure for that compound.

The X-ray single crystal structures for the iodylbenzene derivatives 2b, 2j and 2l were also determined and the ORTEP diagrams are shown in FIGS. 2, 3 and 4.

Example 1

Iodylbenzene (2a)

$^1$H NMR (DMSO-$d_6$): δ 7.92-7.95 (m, 2H, H-2, 6), 7.54-7.56 (m, 3H, H-3, 4, 5).
$^{13}$C NMR (DMSO-$d_6$): δ 150.90 (C-1), 131.44 (C-4), 129.01 (C-3, 5), 126.53 (C-2, 6).
Anal. Calcd for $C_6H_5IO_2$: C, 30.53; H, 2.14. Found: C, 30.42; H, 2.07.

Example 2

4-Methyliodylbenzene (2b)

$^1$H NMR (DMSO-$d_6$): δ 7.82 (d, 2H, H-2, 6), 7.38 (d, 2H, H-3, 5), 2.36 (s, 3H, $CH_3$).
$^{13}$C NMR (DMSO-$d_6$): δ 147.86 (C-1), 141.55 (C-4), 129.50 (C-3, 5), 126.54 (C-2, 6), 20.99 ($CH_3$).
MS (ESI) Calcd for $C_7H_7IO_2$ ($M^+$): 249.95. Found: 272.8 ($M^+$+Na).
Anal. Calcd for $C_7H_7IO_2$: C, 33.63; H, 2.82. Found: C, 33.68; H, 2.79.
See FIG. 2 which shows 4-methyliodylbenzene (2b) and the single crystal X-ray structure for that compound.

Example 3

4-Chloroiodylbenzene (2c)

$^1$H NMR (DMSO-$d_6$): δ 7.95 (d, 2H, H-2, 6), 7.63 (d, 2H, H-3, 5).
$^{13}$C NMR (DMSO-$d_6$): δ 149.71 (C-1), 136.15 (C-4), 128.78 (C-3, 5), 128.55 (C-2, 6).
MS (ESI) Calcd for $C_6H_4O_2ClI$ ($M^+$): 269.89. Found: 292.8 ($M^+$+Na).

Example 4

4-Phenyliodylbenzene (2d)

$^1$H NMR (DMSO-$d_6$): δ 7.38-8.05 (m, 9H, ArH).
MS (ESI) Calcd for $C_{12}H_9IO_2$ ($M^+$): 311.96. Found: 334.9 ($M^+$+Na).

Example 5

3-Acetyliodylbenzene (2e)

$^1$H NMR (DMSO-$d_6$): δ 8.53 (t, 1H, H-2), 8.20 (dt, 1H, H-6), 8.12 (dt, 1H, H-4), 7.73 (t, 1H, H-5), 2.63 (s, 3H, $COCH_3$).
$^{13}$C NMR (DMSO-$d_6$): δ 197.65 (CO), 152.35 (C-1), 137.47 (C-3), 131.52 (C-4, 6), 129.78 (C-5), 126.50 (C-2).
MS (ESI) Calcd for $C_8H_7IO_3$ ($M^+$): 277.94. Found: 300.8 ($M^+$+Na).

Example 6

4-Acetyliodylbenzene (2f)

$^1$H NMR (DMSO-$d_6$): δ 8.07 (q, 4H, H-2, 3, 5, 6), 2.61 (s, 3H, $COCH_3$).
$^{13}$C NMR (DMSO-$d_6$): δ 197.76 (CO), 155.69 (C-1), 138.69 (C-4), 128.53 (C-3, 5), 126.88 (C-2, 6).

Example 7

4-Formyliodylbenzene (2g)

$^1$H NMR (DMSO-$d_6$): δ 8.02 (d, 2H, H-2, 6), 7.67 (d, 2H, H-3, 5).

$^{13}$C NMR (DMSO-$d_6$): δ 193.40 (CHO), 157.45 (C-1), 138.24 (C-4), 130.20 (C-3, 5), 127.79 (C-2, 6).

MS (ESI) Calcd for $C_7H_5IO_3$ (M$^+$): 263.93. Found: 262.8 (M$^+$−1).

Example 8

1-Iodyl-4-ethylbenzoate (2h)

$^1$H NMR (DMSO-$d_6$): δ 8.11 (m, 4H, H-2, 3, 5, 6), 4.35 (q, 2H, CH$_2$), 1.34 (t, 3H, CH$_3$).

$^{13}$C NMR (DMSO-$d_6$): δ 165.60 (COO), 156.36 (C-1), 132.59 (C-4), 129.92 (C-3, 5), 127.45 (C-2, 6), 61.65 (CH$_2$), 14.59 (CH$_3$).

Example 9

4-Cyanoiodylbenzene (2i)

$^1$H NMR (DMSO-$d_6$): δ 8.13 (dt, 2H, H-2, 6), 8.03 (dt, 2H, H-3, 5).

$^{13}$C NMR (DMSO-$d_6$): δ 156.57 (C-1), 133.09 (C-3, 5), 127.98 (C-2, 6), 118.66 (CN), 114.02 (C-4).

MS (ESI) Calcd for $C_7H_4INO_2$ (M$^+$): 260.93. Found: 283.8 (M$^+$+Na).

Example 10

2-Nitroiodylbenzene (2j)

$^1$H NMR (DMSO-$d_6$): δ 8.36 (d, 1H, H-3), 8.27 (dd, 1H, H-6), 8.18 (t, 1H, H-5), 7.88 (t, 1H, H-4).

$^{13}$C NMR (DMSO-$d_6$): δ 144.06 (C-2), 143.72 (C-1), 136.70 (C-5), 132.93 (C-4), 125.11 (C-6), 124.90 (C-3).

$^{15}$N NMR (DMSO-$d_6$): δ 369.30.

MS (ESI) Calcd for $C_6H_4INO_4$ (M$^+$): 280.92. Found: 303.8 (M$^+$+Na).

Example 11

3-Nitroiodylbenzene (2k)

$^1$H NMR (DMSO-$d_6$): δ 8.77 (t, 1H, H-2), 8.37 (m, 2H, H-4, 6), 7.85 (t, 1H, H-5).

$^{13}$C NMR (DMSO-$d_6$): δ 152.82 (C-1), 147.38 (C-3), 133.10 (C-6), 130.33 (C-5), 125.78 (C-4), 121.62 (C-2).

$^{15}$N NMR (DMSO-$d_6$): δ 369.20.

MS (ESI) Calcd for $C_6H_4INO_4$ (M$^+$): 280.92. Found: 303.8 (M$^+$+Na).

See FIG. 3 which shows 2-nitroiodylbenzene (2j) and the single crystal X-ray structure for that compound.

Example 12

4-Nitroiodylbenzene (2l)

$^1$H NMR (DMSO-$d_6$): δ 8.37 (d, 2H, H-3, 5), 8.20 (d, 2H, H-2, 6).

$^{13}$C NMR (DMSO-$d_6$): δ 157.72 (C-1), 149.02 (C-4), 128.11 (C-2, 6), 123.70 (C-3, 5).

$^{15}$N NMR (DMSO-$d_6$): δ 370.10.

MS (ESI) Calcd for $C_6H_4INO_4$ (M$^+$): 280.92. Found: 303.9 (M$^+$+Na).

See FIG. 4 which shows 4-nitroiodylbenzene (2l) and the single crystal X-ray structure for that compound.

Example 13

2-Methyl-4-Nitroiodylbenzene (2m)

$^1$H NMR (DMSO-$d_6$): δ 8.30 (m, 1H, H-5), 8.20 (m, 1H, H-3), 8.10 (m, 1H, H-6).

$^{13}$C NMR (DMSO-$d_6$): δ 156.50 (C-1), 149.62 (C-4), 139.28 (C-2), 126.16 (C-6), 125.90 (C-3), 121.94 (C-5).

$^{15}$N NMR (DMSO-$d_6$): δ 369.66.

MS (ESI) Calcd for $C_6H_4INO_4$ (M$^+$): 294.93. Found: 318.0 (M$^+$+Na).

Figure 5:
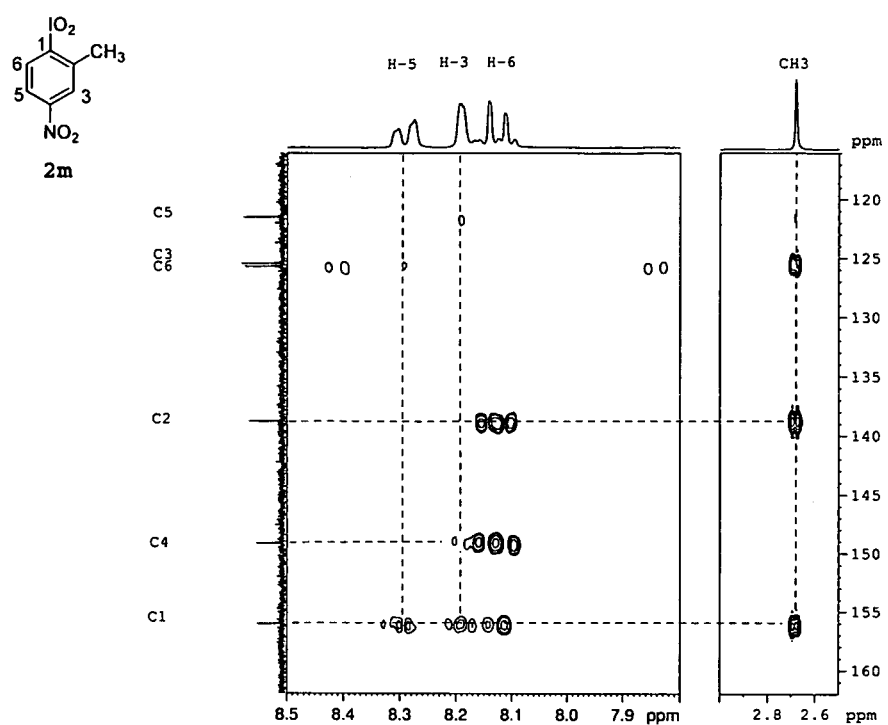
FIG. 5 shows 2-methyl-4-nitroiodylbenzene (2m) and the C-13/H-1 two dimensional (2D) Heteronuclear Multiple Bond Correlation (HMBC) NMR spectrum of that compound.
Figure 6:
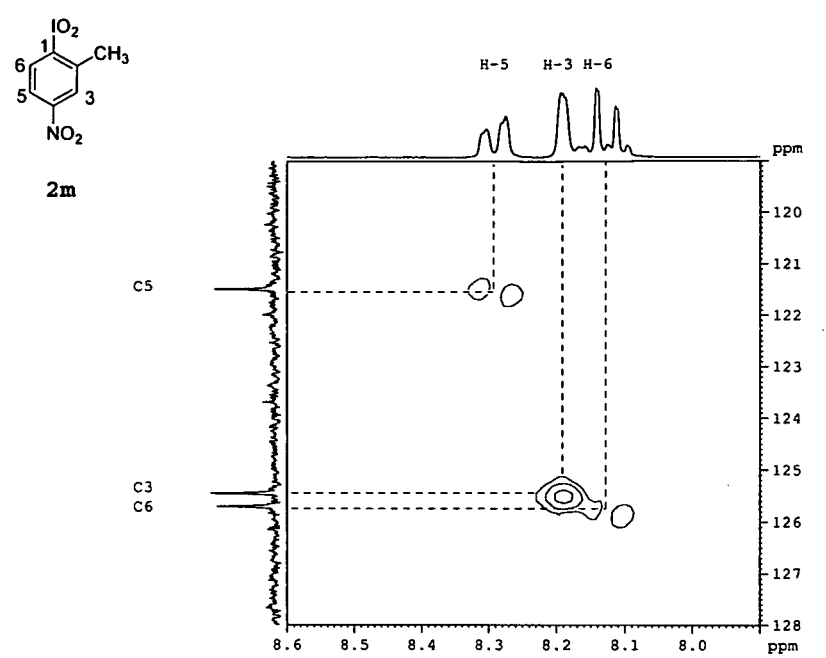
FIG. 6 shows 2-methyl-4-nitroiodylbenzene (2m) and the C-13/H-1 two dimensional (2D) Heteronuclear Multiple Quantum Coherence (HMQC) NMR spectrum of that compound.
Figure 7:
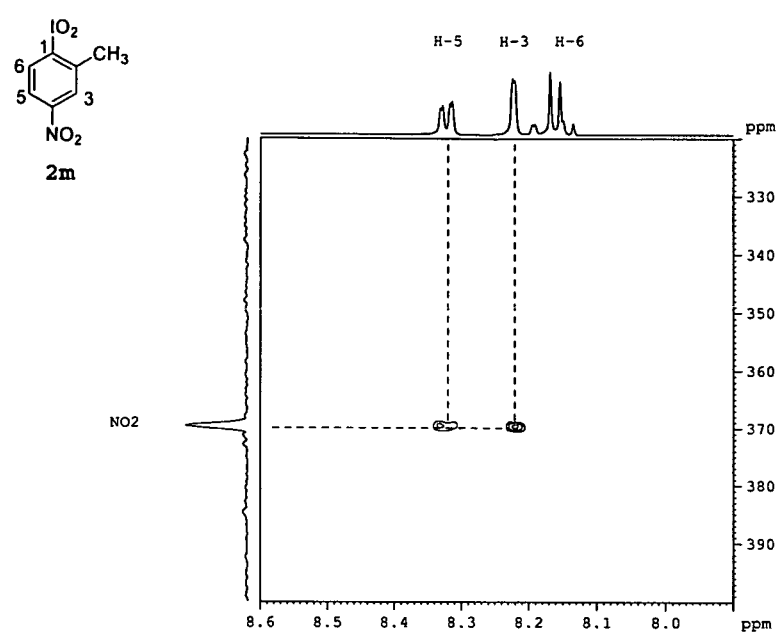
FIG. 7 shows 2-methyl-4-nitroiodylbenzene (2m) and the N-15/H-1 HMBC NMR spectrum of that compound.
Figure 8:
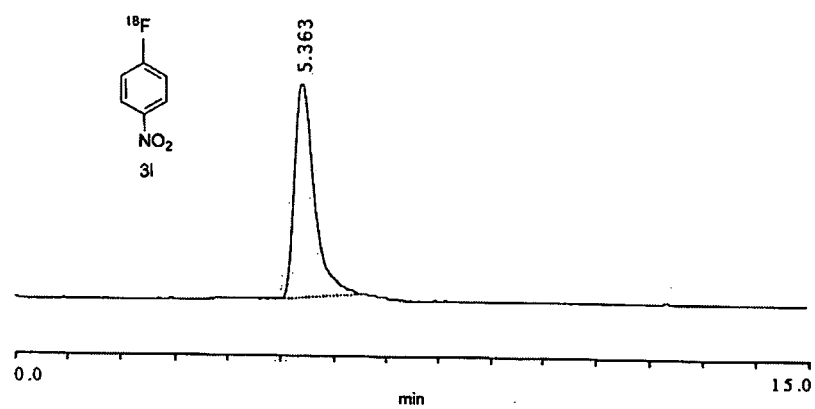
FIG. 8 shows the test conditions and the analytical radio HPLC trace of the crude product of the reaction of an iodylbenzene derivative with no-carrier-added [F-18]fluoride ion. In this particular case, 4-nitro-[F-18]fluorobenzene (3l) was obtained by the radiofluorination of the corresponding iodyl precursor 2l.
Figure 9:
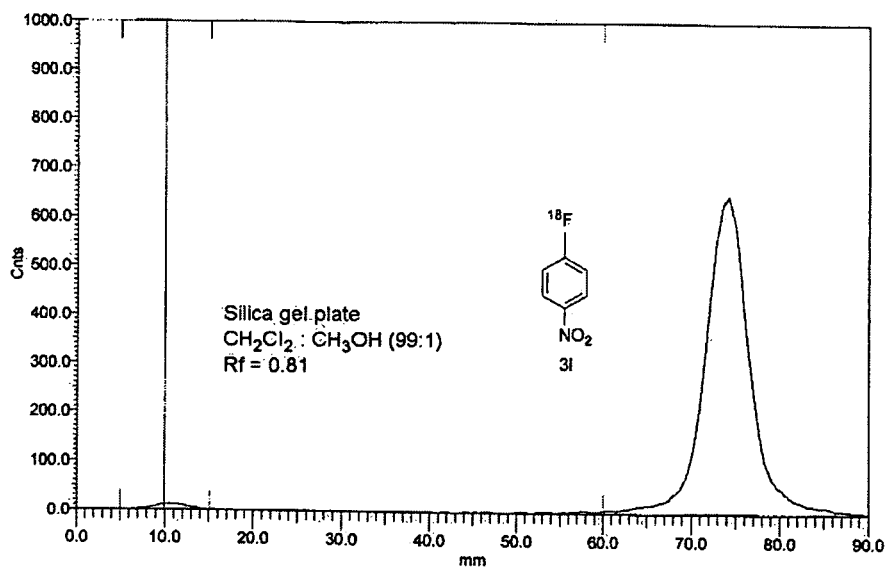
FIG. 9 shows the radio TLC trace of the crude product of the reaction of 4-nitroiodylbenzene (2l) with no-carrier-added [F-18]fluoride ion.

See FIGS. 5, 6 and 7. The C-13/H-1 two dimensional (2D) Heteronuclear Multiple Bond Correlation (HMBC) NMR spectrum, the C-13/H-1 two dimensional (2D) Heteronuclear Multiple Quantum Coherence (HMQC) NMR spectrum and the N-15/H-1 HMBC NMR spectrum of this compound are provided. This 2D NMR technique permits an unequivocal assignment of C-13/H-1 NMR signals thereby establishing the structure of the compound.

Example 14

3-Iodylpyridine (2n)

$^1$H NMR (DMSO-$d_6$): δ 9.00 (d, 1H, H-2), 8.69 (dd, 1H, H-6), 8.26 (dt, 1H, H-4), 7.60 (m, 1H, H-5).

$^{13}$C NMR (DMSO-$d_6$): δ 152.01 (C-6), 148.24 (C-2), 148.05 (C-3), 134.85 (C-4), 124.96 (C-5).

MS (ESI) Calcd for $C_5H_4INO_2$ (M$^+$): 311.96. Found: 334.9 (M$^+$+Na).

The reaction of iodyl (IO$_2$)-containing benzene derivatives with fluoride ion is not shown or suggested in the prior art. In the reaction described herein, a number of iodylbenzene derivatives have been reacted, for the first time, with no-carrier-added [F-18] fluoride ion to produce F-18 labeled aryl analogs. The [F-18]fluoride ion regiospecifically substitutes the iodyl group on the aromatic ring.

In a first embodiment, conditions used for the radiolabeling reaction are as follows: No-carrier-added [F-18]fluoride ion was produced by proton bombardment of [O-18]water in a cyclotron target body. No fluorine moieties other than [F-18] ion are produced. The aqueous [F-18]fluoride ion was treated with 1.0 mg of potassium carbonate and 10 mg of Kryptofix 2.2.2.® compound to form an aqueous solution. Kryptofix 2.2.2.® compound is one example of a family of synthetic bi- and polycyclic multidentate ligands capable of encapsulating a variety of cations, referred to generically as cryptands. Kryptofix 222® is 4,7,13,16,21,24-Hexaoxa-1,10-diazabicyclo[8.8.8]-hexacosane ($C_{18}H_{36}N_2O_6$) with the following chemical structure:

MS (ESI) Calcd for $C_8H_7IO_3$ (M$^+$): 277.94. Found: 300.8 (M$^+$+Na).

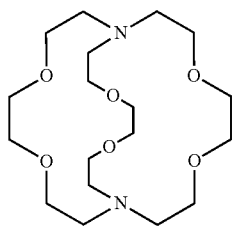 [SMILES: C1COCCN2CCOCCOCCN(CCO1)CCOCCOCC2]

The aqueous solution was evaporated at 100-120° C. and the residue was further dried by azeotropic distillation with acetonitrile. Alternatively, dry no-carrier-added [F-18] CsF or quaternary ammonium [F-18]fluorides (e.g., Me$_4$NF, Et$_4$NF, n-Bu$_4$NF, (PhCH$_2$)$_4$NF) can be used in the place of [F-18] KF/Kryptofix complex for the nucleophilic substitution reaction described above. Dry no-carrier-added [F-18]CsF is prepared by treating Cs$_2$CO$_3$ (1 mg) with [F-18] fluoride ion prepared by the proton irradiation of [O-18] water and evaporating the water as an azeotrope with acetonitrile. Quaternary ammonium [F-18] fluorides are similarly prepared from the corresponding bicarbonate salts.

An iodylbenzene derivative 2a-n (2 to 17 mg), as shown in FIG. 1, was dissolved in dry DMSO (1 mL) and added to the dried no-carrier-added potassium [F-18]fluoride/Kryptofix complex, Cs$^{18}$F or a [F-18] quaternary ammonium fluoride as prepared above. The reaction vessel was then hermetically sealed with a glass or silicone stopper and heated to a temperature between 110°-190° C. for 10-30 min. The reaction mixture was cooled to room temperature and transferred to a silica gel chromatography column (12×1 cm) where it was equilibrated with diethyl ether. The column, upon elution with 10-15 mL of ether, provided the [F-18]fluorobenzene derivatives as evidenced by radioHPLC and radioTLC analyses. Alternatively, the reaction mixture can be processed using a Waters Corporation C-18 Sep-Pak® instead of the silica gel column. If the C-18 Sep-Pak® is used, the reaction mixture was diluted with 10 mL of water and passed through the C-18 Sep-Pak® pre-equilibrated with methanol (5 mL) followed by water (10 mL). The Sep-Pak® was flushed with water (10 mL) and the product was eluted out with 2 mL of methanol. The crude product recovered by either method was found to ≥95% radiochemically pure. However, ≥99% radiochemically and chemically pure product was obtained by semi-preparative HPLC purification of the crude reaction mixture using silica or C-18 HPLC columns.

Table 1 lists various iodylbenzene precursors and the F-18 labeled aryl derivatives obtained therefrom using this method along with the radiochemical yields and reaction conditions employed. FIGS. 2-9 illustrate further information regarding compounds 2b, 2j, 2l, 2m and 3l.

TABLE 1

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| 2a (PhIO$_2$) | 5 mg precursor in 1 mL of DMSO; K$^{18}$F/Kryptofix; 130° C./10 min in a sealed vessel. | 3a ($^{18}$F-Ph) | 2.3 |
| 2a (PhIO$_2$) | 11 mg precursor in 1 mL of DMSO; K$^{18}$F/Kryptofix; 190° C./15 min in a sealed vessel. | 3a ($^{18}$F-Ph) | 6.6 |
| 2b (4-CH$_3$-C$_6$H$_4$-IO$_2$) | 5 mg precursor in 1 mL of DMSO; K$^{18}$F/Kryptofix; 130° C./10 min in a sealed vessel. | 3b (4-CH$_3$-C$_6$H$_4$-$^{18}$F) | 0.75 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
|  | 11 mg precursor in 1 mL of DMSO; K$^{18}$F/Kryptofix; 180° C./20 min in a sealed vessel. | 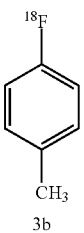<br>3b | 1.3 |
|  | 14 mg precursor in 1 mL of DMSO; K$^{18}$F/Kryptofix; 200° C./20 min in a sealed vessel. | 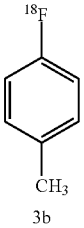<br>3b | 2.4 |
|  | 15 mg precursor in 1 mL of DMSO; K$^{18}$F/Kryptofix; 180° C./30 min in a sealed vessel. | 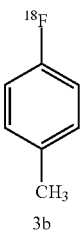<br>3b | 1.1 |
| 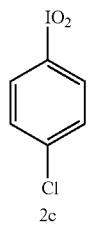<br>2c | 15 mg precursor in 1 mL of DMSO; K$^{18}$F/Kryptofix; 150° C./20 min in a sealed vessel. | 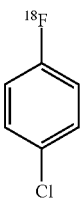<br>3c | 4.1 |
|  | 17 mg precursor in 1 mL of DMSO; K$^{18}$F/Kryptofix; 180° C./20 min in a sealed vessel. | 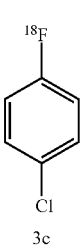<br>3c | 8.4 |
| 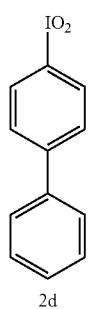<br>2d | ~2 mg precursor in 1 mL of DMSO; K$^{18}$F/Kryptofix; 150° C./10 min in a sealed vessel. | 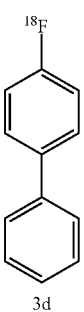 [SMILES: [18F]c1ccc(-c2ccccc2)cc1]<br>3d | 8.9 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| 3-IO$_2$-C$_6$H$_4$-COCH$_3$ (2e) | 15 mg precursor in 1 mL of DMSO; K$^{18}$F/Kryptofix; 180° C./20 min in a sealed vessel. | 3-$^{18}$F-C$_6$H$_4$-COCH$_3$ (3e) | 4.8 |
| 4-IO$_2$-C$_6$H$_4$-COCH$_3$ (2f) | 5 mg precursor in 1 mL of DMSO; K$^{18}$F/Kryptofix; 130° C./10 min in a sealed vessel. | 4-$^{18}$F-C$_6$H$_4$-COCH$_3$ (3f) | 46.2 |
| | 10 mg precursor in 1 mL of DMSO; Cs$^{18}$F; 180° C./20 min in a sealed vessel. | 4-$^{18}$F-C$_6$H$_4$-COCH$_3$ (3f) | 14.3 |
| | 10 mg precursor in 1 mL of DMSO; K$^{18}$F/Kryptofix; 150° C./20 min in a sealed vessel. | 4-$^{18}$F-C$_6$H$_4$-COCH$_3$ (3f) | 50.8 |
| | 12 mg precursor in 1 mL of DMSO; K$^{18}$F/Kryptofix; 150° C./20 min in a sealed vessel. | 4-$^{18}$F-C$_6$H$_4$-COCH$_3$ (3f) | 40.7 |
| 4-IO$_2$-C$_6$H$_4$-CHO (2g) | 6 mg precursor in 1 mL of DMSO; K$^{18}$F/Kryptofix; 180° C./20 min in a sealed vessel. | 4-$^{18}$F-C$_6$H$_4$-CHO (3g) | 76.7 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| 4-(IO$_2$)-C$_6$H$_4$-COOC$_2$H$_5$ <br> 2h | 10 mg precursor in 1 mL of DMSO; K$^{18}$F/Kryptofix; 180° C./20 min in a sealed vessel. | 4-($^{18}$F)-C$_6$H$_4$-COOC$_2$H$_5$ <br> 3h | 86.0 |
| 4-(IO$_2$)-C$_6$H$_4$-CN <br> 2i | 10 mg precursor in 1 mL of DMSO; K$^{18}$F/Kryptofix; 180° C./20 min in a sealed vessel. | 4-($^{18}$F)-C$_6$H$_4$-CN <br> 3i | 86.2 |
| | 5 mg precursor in 1 mL of DMSO; K$^{18}$F/Kryptofix; 130° C./10 min in a sealed vessel. Product isolated with C-18 Sep-Pak. | 4-($^{18}$F)-C$_6$H$_4$-CN <br> 3i | 45.0 |
| | 5 mg precursor in 1 mL of DMSO; K$^{18}$F/Kryptofix; 110° C./10 min in a sealed vessel. Product isolated with silica gel column and ether elution. | 4-($^{18}$F)-C$_6$H$_4$-CN <br> 3i | 47.0 |
| | 5 mg precursor in 1 mL of DMSO; K$^{18}$F/Kryptofix; 130° C./10 min in a sealed vessel. Product isolated with silica gel column and ether elution. | 4-($^{18}$F)-C$_6$H$_4$-CN <br> 3i | 77.3 |
| | 5 mg precursor in 1 mL of DMSO; K$^{18}$F/Kryptofix; 140° C./10 min in a sealed vessel. Product isolated with silica gel column and ether elution. | 4-($^{18}$F)-C$_6$H$_4$-CN <br> 3i | 78.3 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| | 5 mg precursor in 1 mL of DMSO; K$^{18}$F/Kryptofix; 150° C./10 min in a sealed vessel. Product isolated with silica gel column and ether elution. | 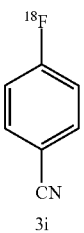<br>3i | 77.9 |
| 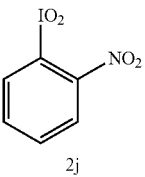<br>2j | 5 mg precursor in 1 mL of DMSO; K$^{18}$F/Kryptofix; 130° C./10 min in a sealed vessel. | 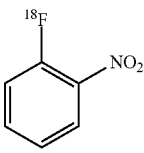<br>3j | 92.4 |
| | 5 mg precursor in 1 mL of DMSO; K$^{18}$F/Kryptofix; 180° C./20 min in a sealed vessel. | 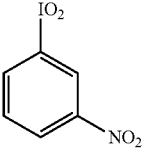<br>3j | 89.5 |
| 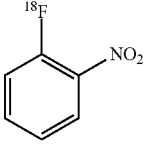<br>2k | 7 mg precursor in 1 mL of DMSO; Cs$^{18}$F; 180° C./20 min in a sealed vessel. | <br>3k | 10.9 |
| | 5 mg precursor in 1 mL of DMSO; K$^{18}$F/Kryptofix; 180° C./20 min in a sealed vessel. | 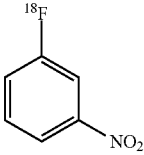<br>3k | 7.8 |
| 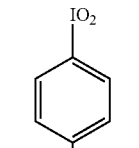<br>2l | 16 mg precursor in 1 mL of DMSO; K$^{18}$F/Kryptofix; 150° C./20 min in a sealed vessel. | 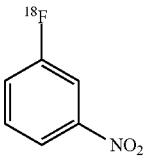<br>3l | 66.4 |
| | 15 mg precursor in 1 mL of DMSO; K$^{18}$F/Kryptofix; 180° C./20 min in a sealed vessel. | 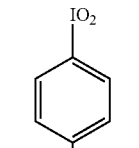<br>3l | 78.8 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| | 5 mg precursor in 1 mL of DMSO; K$^{18}$F/Kryptofix; 150° C./10 min in a sealed vessel. | 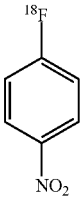 31 | 68.3 |
| | 5 mg precursor in 1 mL of DMSO; K$^{18}$F/Kryptofix; 140° C./10 min in a sealed vessel. | 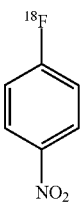 31 | 82.7 |
| | 5 mg precursor in 1 mL of DMSO; K$^{18}$F/Kryptofix; 130° C./10 min in a sealed vessel. | 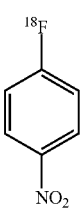 31 | 76.5 |
| | 5 mg precursor in 1 mL of DMSO; K$^{18}$F/Kryptofix; 120° C./10 min in a sealed vessel. | 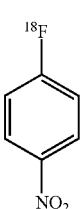 31 | 77.0 |
| | 5 mg precursor in 1 mL of DMSO; K$^{18}$F/Kryptofix; 110° C./10 min in a sealed vessel. | 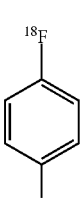 31 | 56.7 |
| | 5 mg precursor in 1 mL of DMSO; K$^{18}$F/Kryptofix; 150° C./10 min in a sealed vessel. | 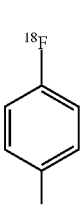 31 | 79.3 |

TABLE 1-continued

Nucleophilic Fluorination of Iodylbenzene Derivatives with [$^{18}$F] Fluoride Ion

| Iodyl Precursor | Reaction Conditions | Product | Radiochemical Yield (%) |
|---|---|---|---|
| 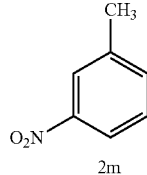 2m | 2 mg precursor in 1 mL of DMSO; K$^{18}$F/Kryptofix; 130° C./10 min in a sealed vessel. | 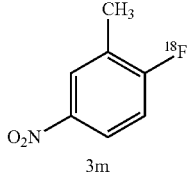 3m | 63.0 |
| | 5 mg precursor in 1 mL of DMSO; K$^{18}$F/Kryptofix; 130° C./10 min in a sealed vessel. | 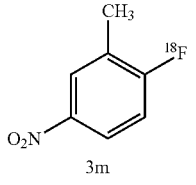 3m | 82.6 |
| 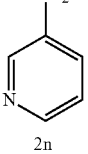 2n | 5 mg precursor in 1 mL of DMSO; K$^{18}$F/Kryptofix; 180° C./20 min in a sealed vessel. | 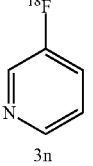 3n | 12.4 |

The results set forth in Table 1 demonstrate the utility and efficiency of the described process. In regard to 3l see FIGS. 8 and 9

The versatility of the fluorination reaction described herein is further detailed in the following representative examples of complex molecule preparation. The synthetic reaction schemes for the preparation of some complex iodyl analogs and their reaction with no-carrier-added [F-18] fluoride ion along with representative two dimensional NMR spectra and selected radio-chromatograms are shown in FIGS. 10-25. These complex F-18 labeled analogs are potential PET imaging agents for certain brain disorders.

Example 15

Figure 10:
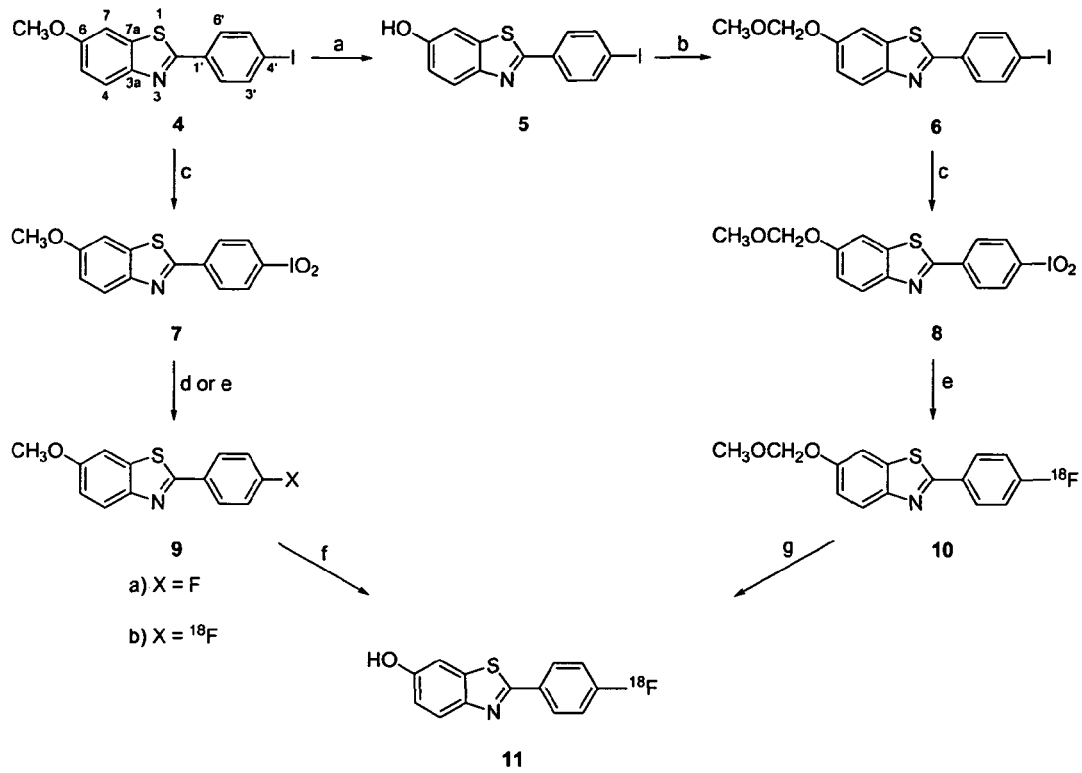
FIG. 10 shows the reaction scheme used for the synthesis of 2-(4-[F-18]fluorophenyl)-6-hydroxy-1,3-benzothiazole (11) involving an iodyl precursor.

The synthetic reaction scheme for the preparation of a complex molecule useful in PET imaging of brain amyloid in Alzheimer's disease patients is given in FIG. 10 and the experimental procedures are furnished below:

a) 2-(4-Iodophenyl)-6-methoxy-1,3-benzothiazole (4)

2-Amino-5-methoxythiophenol was prepared as set forth in C. A. Mathis, Y. Wang, D. P. Holt, G-F. Huang, M. L. Debnath and W. E. Klunk, "Synthesis and Evaluation of $^{11}$C-Labeled 6-Substituted 2-Arylbenzothiazoles as Amyloid Imaging Agents." *J. Med. Chem.*, 46, pp 2740-2754 (2003). 4-Iodobenzyl chloride (5.0 g, 18.8 mmol) was added to a hot solution of 2-amino-5-methoxythiophenol (2.32 g, 15.0 mmol) in toluene (75 mL) and the reaction mixture was stirred at 100° C. for 1 h. Methanol (1 mL) was then added to destroy the excess 4-iodobenzoyl chloride. The hot toluene solution was then passed through a pad of silica gel (~15 g) in a Buchner funnel. The silica gel was rinsed a few more times with hot toluene. The filtrate upon concentration gave pure 2-(4-iodophenyl)-6-methoxy-1,3-benzothiazole (4) (1.65 g, 40%) as off-white crystals.

$^1$H NMR (DMSO-d$_6$): δ 7.94 (d, J=8.8 Hz, 1H, H-4), 7.81 (m, J$_{AB}$=8.6 Hz, 2H, H-3', 5'), 7.91 (m, J$_{AB}$=8.6 Hz, 2H, H-2', 6'), 7.72 (d, J=2.5 Hz, 1H, H-7), 7.13 (dd, J=8.9, 2.6 Hz, 1H, H-5), 3.84 (s, 3H, OCH$_3$).

$^{13}$C NMR (DMSO-d$_6$): δ 164.1 (C-2), 158.1 (C-6), 148.4 (C-3a), 138.6 (C-3', 5'), 136.5 (C-7a), 133.0 (C-1'), 129.0 (C-2', 6'), 124.0 (C-4), 116.6 (C-5), 105.3 (C-7), 98.5 (C-4'), 55.2 (CH$_3$O).

b) 2-(4-Iodophenyl)-1,3-benzothiazol-6-ol (5)

Boron tribromide (1 M in CH$_2$Cl$_2$, 6 mL) was added to an anhydrous CH$_2$Cl$_2$ (20 mL) solution of 4 (550 mg, 1.5 mmol). After stirring at room temperature for 24 h, the reaction mixture was quenched with ice water (10 mL) and neutralized with solid NaHCO$_3$ (1.51 g, 18.0 mmol). The mixture was diluted with pH 7 buffer solution (Fisher, 20 mL) and extracted with dichloromethane-methanol (4:1, 3×100 mL). The extracts were combined, dried with anhydrous Na$_2$SO$_4$, and evaporated. The residue was treated with CH$_2$Cl$_2$/MeOH, to give pure 2-(4-iodophenyl)-1,3-benzothiazol-6-ol (5) as a white solid (295 mg, 55.8%).

$^1$H NMR (DMSO-d$_6$): δ 9.95 (s, 1H, OH), 7.78 (m, J$_{AB}$=8.4 Hz, 2H, H-3', 5'), 7.85 (d, J=8.8 Hz, 1H, H-4), 7.90 (m, J$_{AB}$=8.4 Hz, 2H, H-2', 6'), 7.41 (d, J=2.4 Hz, 1H, H-7), 6.99 (dd, J=8.8, 2.4 Hz, 1H, H-5).

$^{13}$C NMR (DMSO-d$_6$): δ 162.5 (C-2), 156.0 (C-6), 147.0 (C-3a), 138.2 (C-3', 5'), 136.1 (C-7a), 132.7 (C-1'), 128.5 (C-2', 6'), 123.6 (C-4), 116.4 (C-5), 106.9 (C-7), 97.7 (C-4').

c) 2-(4-Iodophenyl)-6-(methoxymethyl)-1,3-benzothiazole (6)

Sodium hydride (60% dispersion in mineral oil; 30 mg, 0.76 mmol) was added to a DMF (2 mL) solution of 5 (225 mg, 0.64 mmol), cooled in an ice bath. After stirring at 0° C. for 1 h, chloromethyl methyl ether (100 μL, 1.33 mmol) and triethylamine (0.2 mL) were added. The reaction mixture was stirred at room temperature overnight and evaporated under reduced pressure. The residue was dissolved in dichloromethane and washed with pH 7 buffer solution (10 mL). The organic phase was dried with anhydrous $Na_2SO_4$, filtered, and evaporated to give the crude product. The crude product was purified by flash chromatography on silica gel ($CH_2Cl_2$), to give 2-(4-iodophenyl)-6-(methoxymethyl)-1,3-benzothiazole (6) (237 mg, 93.7%) as a white solid.

$^1$H NMR (DMSO-$d_6$): δ 7.96 (d, J=9.0 Hz, 1H, H-4), 7.81 (d, $J_{AB}$=8.1 Hz, 2H, H-3', 5'), 7.91 (d, $J_{AB}$=8.1 Hz, 2H, H-2', 6'), 7.78 (d, J=2.5 Hz, 1H, H-7), 7.22 (dd, J=9.0, 2.5 Hz, 1H, H-5), 5.28 (s, 2H, OCH$_2$O), 3.41 (s, OCH$_3$).

$^{13}$C NMR (DMSO-$d_6$): δ 164.5 (C-2), 155.0 (C-6), 148.9 (C-3a), 138.4 (C-3', 5'), 135.9 (C-7a), 132.5 (C-1'), 128.6 (C-2', 6'), 123.7 (C-4), 117.4 (C-5), 108.3 (C-7), 98.3 (C-4'), 94.4 (OCH$_2$O), 56.0 (CH$_3$O).

d) 2-(4-Iodylphenyl)-6-methoxy-1,3-benzothiazole (7)

A freshly prepared dimethyldioxirane solution (30 mL), as described above (para. [0035]) for the synthesis of simple iodylbenzene analogs, was added drop wise with stirring to an anhydrous dichloromethane (15 mL) solution of 4 (100 mg, 0.28 mmol) cooled in an ice bath. The resultant suspension was stirred at 0° C. for additional period of 2-3 hours and then at room temperature overnight. The yellow solid that was formed was collected by centrifugation and washed three times with dichloromethane. The residue was dried in vacuum to give 2-(4-iodylphenyl)-6-methoxy-1,3-benzothiazole (7) (95.4 mg, 84%) as a beige solid.

$^1$H NMR (DMSO-$d_6$): δ 8.11 (d, $J_{AB}$=8.3 Hz, 2H, H-2', 6'), 8.22 (d, $J_{AB}$=8.3 Hz, 2H, H-3', 5'), 7.98 (d, J=9.0 Hz, 1H, H-4), 7.76 (d, J=2.4 Hz, 1H, H-7), 7.16 (dd, J=9.0, 2.4 Hz, 1H, H-5), 3.86 (s, 3H, OCH$_3$).

$^{13}$C NMR (DMSO-$d_6$): δ 163.5 (C-2), 157.9 (C-6), 153.4 (C-4'), 148.0 (C-3a), 136.4 (C-7a), 135.5 (C-1'), 127.7 (C-3', 5'), 127.2 (C-2', 6'), 123.8 (C-4), 116.4 (C-5), 105.0 (C-7), 55.8 (CH$_3$O).

MS (ESI) Calcd for $C_{14}H_{10}INO_3S$ (M$^+$): 398.94. Found 399.95 (M$^+$+1) and 421.93 (M$^+$+Na).

e) 2-(4-Iodylphenyl)-6-(methoxymethyl)-1,3-benzothiazole (8)

A second portion of the freshly prepared solution of dimethyldioxirane (30 mL) was added drop wise with stirring to an anhydrous dichloromethane (15 mL) solution of 6 (100 mg, 0.25 mmol) cooled in an ice bath. The reaction mixture was stirred at 0° C. for a further period of 2-3 hours and then at room temperature overnight. The yellow solid that was formed was collected by centrifugation. The solid was washed three times with dichloromethane and dried in vacuum to give the iodyl product 2-(4-iodylphenyl)-6-(methoxymethyl)-1,3-benzothiazole (8) (112.8 mg) in near quantitative yield.

$^1$H NMR (DMSO-$d_6$): δ 8.12 (d, $J_{AB}$=8.7 Hz, 2H, H-2', 6'), 8.23 (d, $J_{AB}$=8.7 Hz, 2H, H-3', 5'), 8.01 (d, J=8.8 Hz, 1H, H-4), 7.83 (d, J=2.5 Hz, 1H, H-7), 7.25 (dd, J=8.8, 2.5 Hz, 1H, H-5), 5.28 (s, 2H, OCH$_2$O), 3.41 (s, OCH$_3$).

$^{13}$C NMR (DMSO-$d_6$): δ 164.3 (C-2), 155.3 (C-6), 153.5 (C-4'), 148.7 (C-3a), 136.2 (C-7a), 135.3 (C-1'), 127.6 (C-3', 5'), 127.2 (C-2', 6'), 123.7 (C-4), 117.4 (C-5), 108.1 (C-7), 94.4 (OCH$_2$O), 55.7 (CH$_3$O).

MS (ESI) Calcd for $C_{15}H_{12}INO_4S$ (M$^+$): 428.95. Found 451.94 (M$^+$+Na).

f) 2-(4-Fluorophenyl)-6-methoxy-1,3-benzothiazole (9a)

A solution of Kryptofix® 2.2.2 (23.4 mg, 0.062 mmol) in acetonitrile (2 mL) was added to a solution of KF (7.3 mg, 0.125 mmol) in water (0.5 mL). The solvents were evaporated at 120° C. and the residue was dried by azeotropic distillation with acetonitrile (3×1 mL). A solution of the iodyl precursor 2-(4-iodylphenyl)-6-methoxy-1,3-benzothiazole (7) (5.2 mg, 0.0125 mmol; dried over P$_2$O$_5$ under high vacuum for 2 hours before use) in hot DMSO (0.5 mL) was added to the dried KF-Kryptofix® complex. The reaction mixture was stirred at 120° C., 150° C. or 180° C. for 10 min. The reaction mixture was cooled and diluted with ice water (3 mL) and passed through a C-18 Sep-Pak® pre-activated with methanol (5 mL) followed by water (10 mL). The Sep-Pak was flushed with water (2×5 mL) and the crude product 9a retained on the Sep-Pak® was eluted off with CH$_2$Cl$_2$ (2×5 mL). The dichloromethane eluent was quantitatively analyzed by analytical HPLC (Waters Symmetry C18 column, 5μ particle size, 150× 4.6 mm; eluent: MeCN/H$_2$O 1:1; flow rate: 1 mL/min; UV 325 nm or 254 nm; R$_t$=27 min) using an authentic sample of 2-(4-fluorophenyl)-6-methoxy-1,3-benzothiazole (9a) as a standard and the yield of the fluoro product 9a formed at 120° C., 150° C. and 180° C. was determined as 6.5%, 3.4% and 34.6%, respectively. The authentic sample of 9a was prepared in accordance with the nucleophilic displacement method for synthesis of non-rigid PBZ polymers described in U.S. Pat. No. 5,104,960.

g) Preparation of 2-(4-[F-18]fluorophenyl)-6-hydroxy-1,3-benzothiazole (11) from the precursors 2-(4-Iodylphenyl)-6-methoxy-1,3-benzothiazole (7) and 2-(4-Iodylphenyl)-6-(methoxymethyl)-1,3-benzothiazole (8)

No-carrier-added [F-18]fluoride ion was produced by proton bombardment of [O-18]water in a cyclotron target body. The aqueous [F-18]fluoride ion was treated with 1.0 mg of potassium carbonate and 10 mg of Kryptofix® 2.2.2. The aqueous solution was evaporated at 120° C. and the residue was dried by azeotropic distillation with acetonitrile. Five milligrams of either the iodyl derivative 7 or iodyl derivative 8 was dissolved in dry DMSO (0.5 mL) and added to the dried potassium [F-18]fluoride/Kryptofix® complex as prepared as described above. The reaction mixture was heated at 150° C. for 10 min and then cooled to room temperature and diluted by the addition of 3 mL of ice water. The diluted mixture was passed through a C-18 Sep-Pak® pre-equilibrated with methanol (5 mL) followed by water (10 mL). The Sep-Pak® was flushed with water (10 mL) and the iodyl derivative 7 or iodyl derivative 8 now F-18 labeled (9b and 10, respectively) was eluted out with 2 mL of dichloromethane. The dichloromethane was evaporated with a stream of nitrogen gas and the residue was subjected to acid hydrolysis and semi-preparative HPLC purification as described below.

h) Acid hydrolysis of F-18 labeled intermediate 2-(4-[F-18]fluorophenyl)-6-methoxy-1,3-benzothiazole (9b) with HI Fifty four percent HI (1 mL, redistilled from red phosphorous) was added to 2-(4-[F-18] fluorophenyl)-6-methoxy-1, 3-benzothiazole (9b) produced from the iodyl precursor 7 and the resultant mixture was heated at 130° C. for 30 min. The reaction mixture was then diluted with acetone (1 mL), neutralized with NaOH (8 M, 0.8 mL) and subjected to semi-preparative HPLC purification (Waters Symmetry C18 column, 300×7.8 mm, particle size: 7μ; MeCN/H$_2$O 4:6, flow rate: 6 mL/min; radioactivity and 254 nm UV detection). The chemically and radiochemically pure 2-(4-[F-18]fluorophenyl)-6-hydroxy-1,3-benzothiazole (11) product that eluted off the HPLC column with a retention time of 11 min was collected and the solvents removed in a rotary evaporator. The residue was co-evaporated with injectable ethanol (2 mL) and then dissolved in 0.7 mL of injectable ethanol and diluted with sterile normal saline (10 mL). The saline solution was sterilized by passing through a 0.22μ Millipore filter into a sterile multi-dose vial. The 2-(4-[F-18]fluorophenyl)-6-hydroxy-1,3-benzothiazole (11) was obtained in 49.3% radiochemical yield (corrected for radioactive decay) with a synthesis time of 120 min.

i) Acid hydrolysis of F-18 labeled intermediate 2-(4-[F-18]fluorophenyl)-6-(methoxymethyl)-1,3-benzothiazole (10) with HCl Thirty seven percent HCl in MeOH (1:2, 0.5 mL) was added to the F-18 labeled intermediate 10 obtained from 2-(4-iodylphenyl)-6-(methoxymethyl)-1,3-benzothiazole (8) and the mixture was heated at 120° C. for 5 min. The acidic solution was then diluted with MeOH (1 mL) and neutralized with NaOAc (2 M solution in water, 1 mL). The chemically and radiochemically pure 2-(4-[F-18]fluorophenyl)-6-hydroxy-1,3-benzothiazole (11) was isolated by semi-preparative HPLC in the same manner as described above to provide a 63.0% radiochemical yield (corrected for radioactive decay).

The usefulness and the versatility of the no-carrier-added nucleophilic F-18 fluorination reaction involving the iodylbenzene derivatives can be illustrated by extending the technique to the synthesis of a variety of F-18 labeled aromatic amino acids and related analogs as exemplified by the preparation of 6-[F-18]fluoro-L-dopa. 6-[F-18]Fluoro-L-dopa, for instance, is a very promising biomarker for PET imaging of movement disorders (e.g. Parkinson disease) in humans. It also finds extensive use in brain tumor imaging with PET. A variety of complex iodyl derivatives as precursors for the synthesis of 6-[F-18]fluoro-L-dopa and its related amino acids and derivatives have been synthesized for the first time. These iodyl precursors were also reacted with no-carrier-added [F-18] fluoride ion to produce the corresponding amino acids and their derivatives. Representative examples of these analogs are provided below:

Example 16

Figure 11:
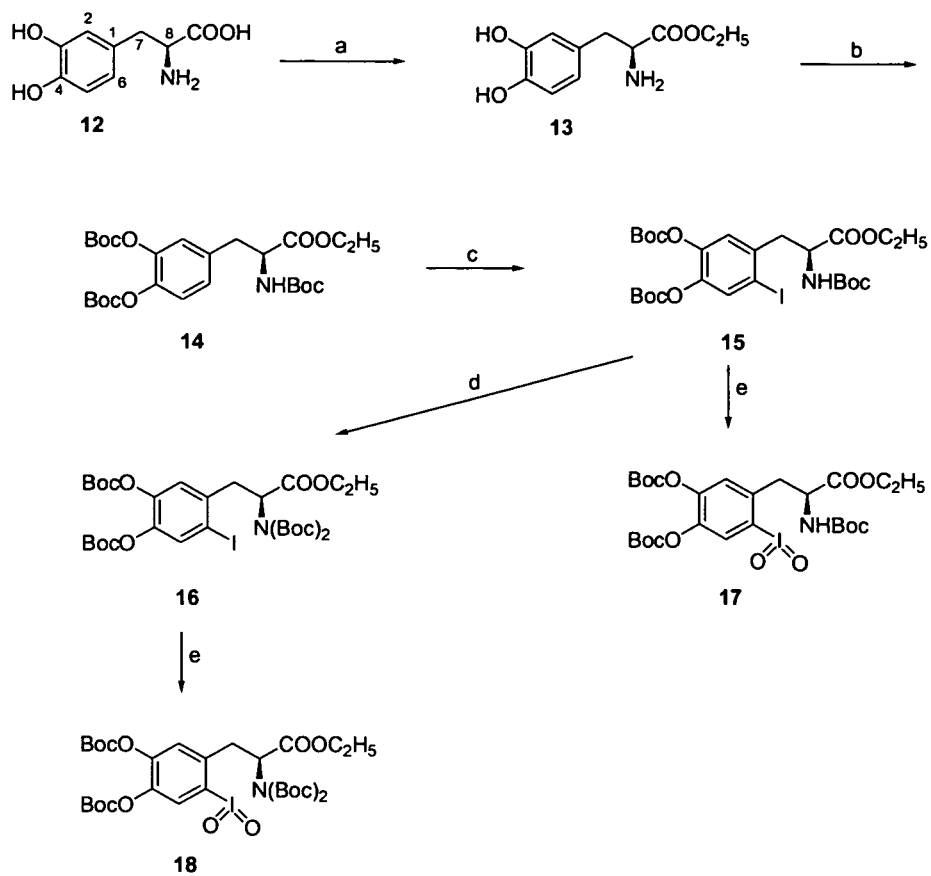
FIG. 11 shows the reaction scheme employed for the synthesis of two different iodyl precursors, namely N-(tert-butoxycarbonyl)-3,4-di(tert-butoxycarbonyloxy)-6-iodyl-L-phenylalanine ethyl ester (17) and N-di-(tert-butoxycarbonyl)-3,4-di(tert-butoxycarbonyloxy)-6-iodyl-L-phenylalanine ethyl ester (18) for the preparation of 6-[F-18]fluoro-L-dopa (32).
Figure 13:
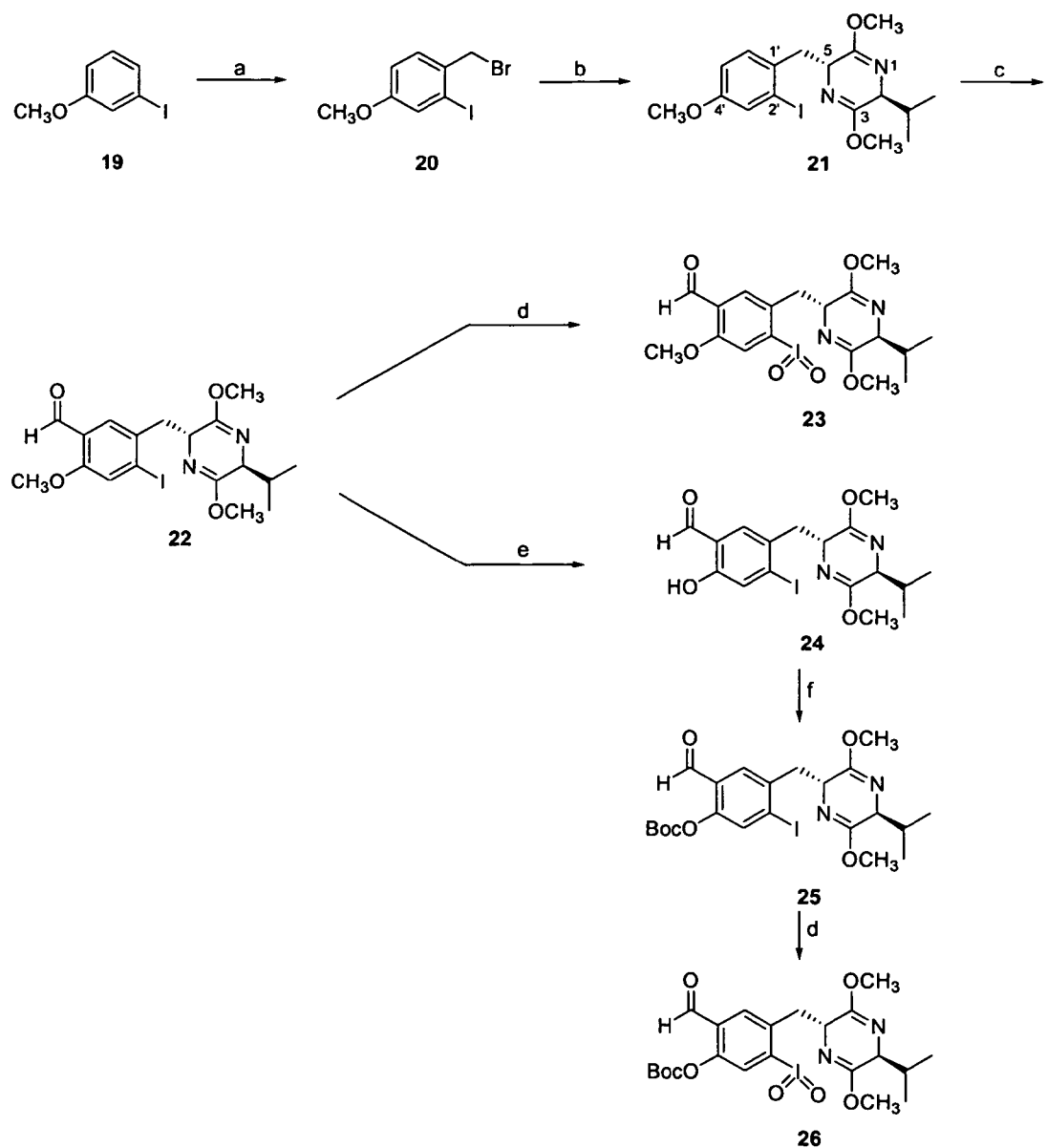
FIG. 13 shows the reaction scheme utilized for the synthesis of an iodyl precursor based on a chiral pyrazine derivative, namely 2,5-dihydro-3,6-dimethoxy-2-isopropyl-5-(2'-iodyl-4'-methoxy-5'-formylbenzyl)-(2R,5S)-pyrazine (23) for the preparation of 6-[F-18]fluoro-L-dopa (32).
Figure 18:
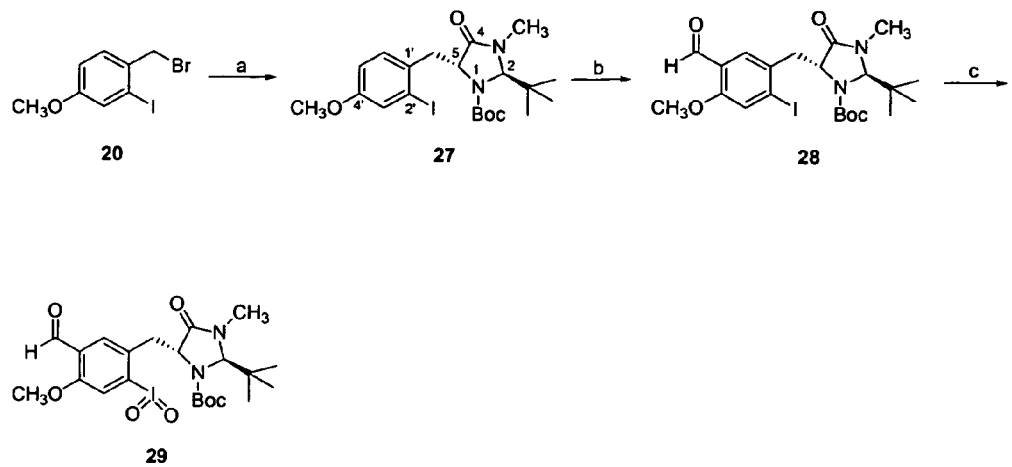
FIG. 18 shows the reaction scheme used for the preparation of a chiral imidazolidinone intermediate, namely (2S,5S)-tert-butyl-5-(2'-iodo-4'-methoxy-5'-formylbenzyl)-2-tert-butyl-3-methyl-4-oxoimidazolidine-1-carboxylate (28).

The details of the synthesis of iodyl precursors for the preparation of 6-[F-18]fluoro-L-dopa are shown in FIGS. 11, 13 and 18. Preparation of N-(tert-butoxycarbonyl)-3,4-di(tert-butoxycarbonyloxy)-6-iodyl-L-phenylalanine ethyl ester (17) and N-di-(tert-butoxycarbonyl)-3,4-di(tert-butoxycarbonyloxy)-6-iodyl-L-phenylalanine ethyl ester (18) from L-dopa (12), shown in FIG. 11, is as follows:

a) 3,4-Dihydroxy-L-phenylalanine ethyl ester (13)

Standard Fisher esterfication of L-dopa (12) (0.13 mol) in anhydrous ethanol (500 mL) with dry HCl gas provided the ester 13 in quantitative yield.

b) N-(tert-butoxycarbonyl)-3,4-di(tert-butoxycarbonyloxy)-L-phenylalanine ethyl ester (14)

The ester 13 (38 mmol) was dissolved dry DMF (60 mL) under argon and triethylamine (460 mmol) was added under stirring. A solution of di-tert-butyl dicarbonate (153 mmol) in dry DMF (40 mL) was then added drop-wise and the reaction mixture was stirred at room temperature overnight. The solution was diluted with ethylacetate (60 mL) and washed with brine (2×100 mL) followed by water (3×100 mL). The organic layer was dried over anhydrous sodium sulfate, filtered and evaporated to provide N-(tert-butoxycarbonyl)-3,4-di(tert-butoxycarbonyloxy)-L-phenylalanine ethyl ester (14) as a white foam in 97% yield.

$^1$H NMR (CDCl$_3$): δ 7.18 (d, 1H, ArH), 7.03 (s, 1H, ArH), 7.00 (d, 1H, ArH), 5.03 (broad d, 1H, NH), 4.54 (q, 1H), 4.19-4.11 (m, 2H), 3.09 (m, 2H), 1.54 (s, 18H), 1.43 (s, 9H), 1.22 (t, 3H).

$^{13}$C NMR (CDCl$_3$): δ 171.50, 155.08, 150.71, 150.60, 142.29, 141.45, 134.80, 127.19, 124.00, 122.97, 116.41, 83.74, 79.98, 61.54, 60.39, 54.24, 37.55, 21.05, 14.19, 14.08.

MS (MALDI): Calcd for C$_{26}$H$_{39}$NO$_{10}$ (M$^+$): 525.26. Found: 548.07 (M$^+$+Na).

c) N-(tert-butoxycarbonyl)-3,4-di(tert-butoxycarbonyloxy)-6-iodo-L-phenylalanine ethyl ester (15)

Iodine (7.4 mmol) and bis(trifluoroacetoxy)iodobenzene (8.16 mmol) were added to a solution of the tri-boc protected dopa analog 14 (5.7 mmol) in anhydrous dichloromethane (60 mL) under argon. (t-Boc, or Boc, stands for (t)ert-(B)ut(O)xy(c)arbonyl.) The reaction mixture was stirred at room temperature for 40 min and then quenched with a saturated solution of sodium thiosulfate. The organic layer was washed with water (3×10 mL), dried with anhydrous sodium sulfate, filtered and evaporated in rotary evaporator. The product was purified by silica gel column chromatography using 15-20% ethyl acetate in hexane as the mobile phase to give the iodo analog, N-(tert-butoxycarbonyl)-3,4-di(tert-butoxycarbonyloxy)-6-iodo-L-phenylalanine ethyl ester 15, as white foam in 77% yield.

$^1$H NMR (CDCl$_3$): δ 7.74 (s, 1H, ArH), 7.14 (s, 1H, ArH), 5.08 (broad d, 1H, NH), 4.59 (q, 1H), 4.22-4.12 (m, 2H), 3.20 (m, 2H), 1.55 (s, 18H), 1.42 (s, 9H), 1.22 (t, 3H).

$^{13}$C NMR (CDCl$_3$): δ 171.61, 154.97, 150.25, 150.19, 142.57, 141.50, 138.13, 133.50, 124.24, 95.47, 84.19, 84.07, 80.03, 61.69, 60.40, 53.47, 42.56, 28.27, 27.59, 21.07, 14.03.

MS (MALDI): Calcd for C$_{26}$H$_{38}$INO$_{10}$ (M$^+$): 651.15. Found: 674.00 (M$^+$+Na).

d) N-di(tert-butoxycarbonyl)-3,4-di(tert-butoxycarbonyloxy)-6-iodo-L-phenylalanine ethyl ester (16)

The tri-boc dopa derivative 15 (0.76 mmol) was dissolved in dry THF (5 mL) under argon and 4-(dimethylamino)pyridine (3.8 mmol) and di-tert-butyldicarbonate (2.85 mmol) were added. The reaction mixture was stirred at room temperature overnight. The resulting yellow solution was diluted with ethyl acetate and washed with water (3×30 mL). The ethyl acetate layer was dried with anhydrous sodium sulfate, filtered and evaporated to provide a semi-solid residue. This crude product upon purification by flash chromatography over silica gel with 15-20% ethyl acetate in hexane as eluent gave the tetra boc derivative, N-di(tert-butoxycarbonyl)-3,4-di(tert-butoxycarbonyloxy)-6-iodo-L-phenylalanine ethyl ester 16, in 74% yield as white foam.

¹H NMR (CDCl₃): δ 7.68 (s, 1H, ArH), 7.06 (s, 1H, ArH), 5.24 (q, 1H), 4.24-4.08 (m, 2H), 3.20 (m, 2H), 1.52 (s, 18H), 1.38 (s, 18H), 1.20 (t, 3H).

¹³C NMR (CDCl₃): δ 169.87, 151.76, 150.16, 150.11, 142.48, 141.33, 139.13, 133.24, 124.86, 95.41, 84.07, 83.87, 83.18, 61.53, 57.39, 40.15, 27.86, 27.57, 14.16.

MS (MALDI): Calcd for $C_{31}H_{46}INO_{12}$ (M⁺): 751.21. Found: 774.07 (M⁺+Na).

e) N-(tert-butoxycarbonyl)-3,4-di(tert-butoxycarbonyloxy)-6-iodyl-L-phenylalanine ethyl ester (17)

The iodo tri-boc derivative 15 (202 mg, 0.31 mmol) was dissolved in anhydrous acetone (8.0 mL) and cooled to 0° C. in an ice bath. A freshly prepared solution of dimethyldioxirane (28 mL) was added to the ice cold solution of the iodo compound 15 drop wise. The solution was subsequently stirred for 1 h at the same temperature. The solvent was then evaporated to dryness. The residue was dissolved in chloroform and washed with water. The organic phase was dried with anhydrous sodium sulfate, filtered and the solvent was evaporated to provide N-(tert-butoxycarbonyl)-3,4-di(tert-butoxycarbonyloxy)-6-iodyl-L-phenylalanine ethyl ester (17) as a white solid (191.2 mg, 90%).

¹H NMR (CDCl₃): δ 8.08 (s, 1H, H-5), 7.29 (s, 1H, H-2), 5.91 (br, s, 1H, NH), 4.45-4.61 (m, 1H, CH), 4.06-4.18 (m, 2H, OCH₂), 3.32-3.55 (m, 2H, Ar—CH₂), 1.54 (s, 9H, tert-butyl CH₃), 1.52 (s, 9H, tert-butyl CH₃), 1.39 (s, 9H, tert-butyl CH₃), 1.18 (t, J=7.04 Hz, 3H, CH₃).

¹³C NMR (CDCl₃): δ 171.93 (CO of ester), 155.42 (NCO), 149.93 (OCO), 149.72 (OCO), 146.60 (C-6), 145.87 (C-3), 142.47 (C-4), 135.37 (C-1), 125.94 (C-2), 121.45 (C-5), 84.37 (2× tert-butyl C), 80.61 (tert-butyl C), 62.41 (OCH₂), 54.61 (CH), 35.66 (Ar—CH₂), 28.27 (tert-butyl CH₃), 27.58 (tert-butyl CH₃), 13.95 (CH₃).

MS (MALDI): Calcd for $C_{26}H_{38}INO_{12}$ (M⁺): 683.14. Found: 706.13 (M⁺+Na).

f) N-di-(tert-butoxycarbonyl)-3,4-di(tert-butoxycarbonyloxy)-6-iodyl-L-phenylalanine ethyl ester (18)

A freshly prepared solution of dimethyldioxirane in acetone (30 mL) was added to an ice cold solution of the iodo tetra-boc derivative 16 (200 mg, 0.27 mmol) in anhydrous acetone (8.0 mL). The solution was stirred for 2 h at 0° C. The solvent was then evaporated to dryness to provide N-di-(tert-butoxycarbonyl)-3,4-di(tert-butoxy-carbonyloxy)-6-iodyl-L-phenylalanine ethyl ester (18) as a white solid.

¹H NMR (DMSO-d₆): δ 8.09 (s, 1H, H-5), 7.28 (s, 1H, H-2), 4.92 (dd, 1H, CHCO), 4.16 (dd, 2H, CH₂O), 4.02 and 2.99 (dd, 2H, CH₂Ar), 1.53 (s, 18H, H-Boc), 1.23 (3H, CH₃).

¹³C NMR (CDCl₃): δ 171.78 (CO), 151.19 (N-Boc C=O), 149.80 (O-Boc C=O), 147.27 (C-6), 145.90 (C-3), 142.46 (C-4), 136.31 (C-1), 125.88 (C-2), 121.00 (C-5), 84.24 (O-Boc tert-C), 62.56 (N-Boc tert-C), 59.80 (CH₂), 35.57 (CH), 28.01 (Boc-CH₃), 27.61 (CH₂Ar), 13.99 (CH₃).

MS (MALDI): Calcd for $C_{31}H_{46}INO_{14}$ (M+): 783.19. Found: 805.87 (M⁺+Na).

Figure 12:
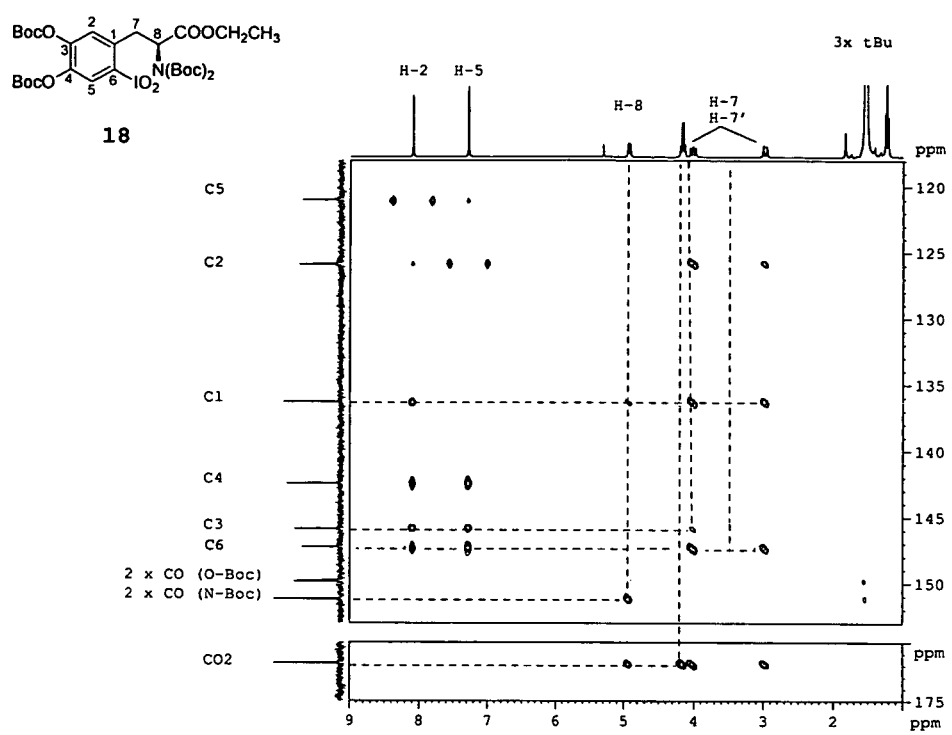
FIG. 12 shows N-di-(tert-butoxycarbonyl)-3,4-di(tert-butoxycarbonyloxy)-6-iodyl-L-phenylalanine ethyl ester (18) and the C-13/H-1 HMBC NMR spectrum of that compound.

The C-13/H-1 HMBC NMR spectrum of compound 18 is shown in FIG. 12. This spectrum permitted the assignment of NMR signals unequivocally for this compound.

Example 17

The details of the synthesis of a second iodyl precursor for 6-[F-18]fluoro-L-dopa shown in FIG. 13, is as follows:

a) 1-(Bromomethyl)-2-iodo-4-methoxybenzene (20)

Bromomethyl methyl ether (5.14 ml, 63.2 mmol) was added to a solution of 3-iodoanisole 19 (7.4 g, 31.6 mmol) in glacial acetic acid (17.0 mL) and the colorless solution was stirred for 2 days at room temperature as set forth in T. J. McCord, D. E. Thornton, K. L. Hulme and A. L. Davis, "Synthesis and Microbiological Properties of 2-Iodotyrosine and Related Compounds." *Texas J. Sci.*, 30, pp 357-363 (1978). The reaction mixture was diluted with water and then extracted with ethyl acetate. The organic phase was dried over Na₂SO₄, filtered and evaporated to produce a yellow oil which was purified by silica gel column chromatography to yield 1-bromomethyl-2-iodo-4-methoxybenzene (20) as a white solid (4.59 g, 45%).

¹H NMR (DMSO-d₆): δ 7.50 (d, 1H, H-6), 7.40 (d, 1H, H-3), 6.90 (dd, 1H, H-5), 4.54 (s, 2H, CH₂), 3.60 (s, 3H, OCH₃).

¹³C NMR (DMSO-d₆): δ 159.50 (C-4), 132.04 (C-1), 131.51 (C-6), 124.40 (C-3), 114.73 (C-5), 101.54 (C-2), 55.58 (CH₃).

MS (ESI) Calcd for $C_8H_8BrIO$ (M⁺): 325.88. Found: 246.96 (M-Br).

Figure 14:
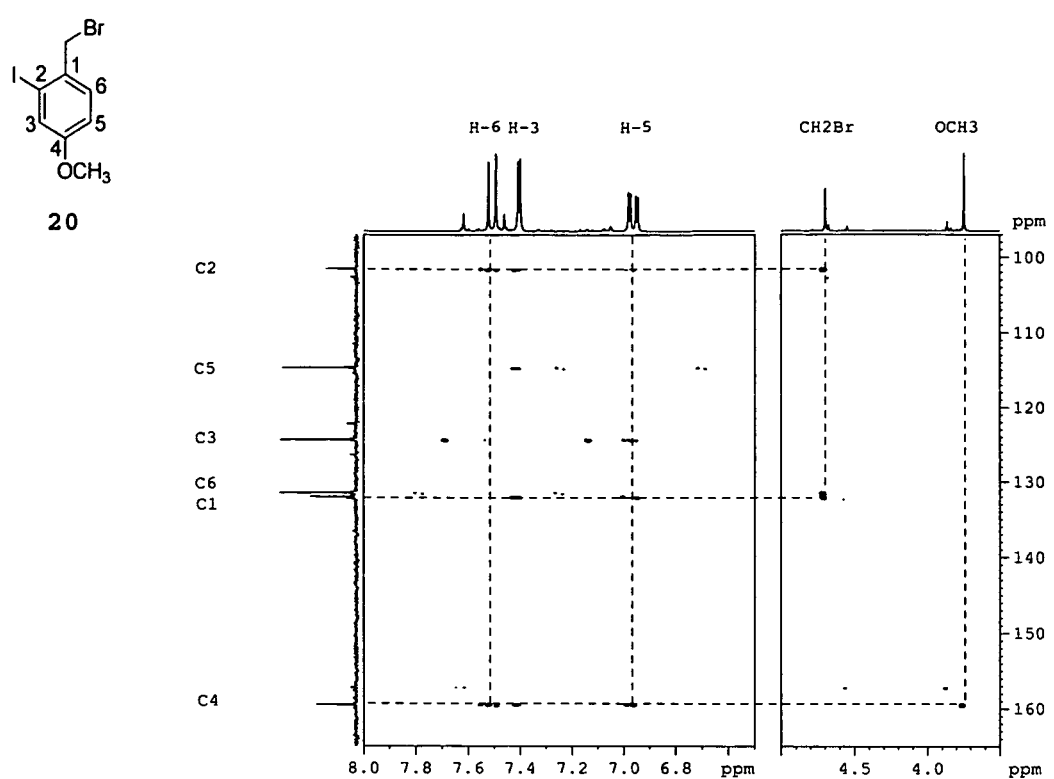
FIG. 14 shows the C-13/H-1 HMBC NMR spectrum of 1-(bromomethyl)-2-iodo-4-methoxybenzene (20).

The C-13/H-1 HMBC NMR spectrum of 1-(bromomethyl)-2-iodo-4-methoxybenzene (20) is shown in FIG. 14.

b) 2,5-Dihydro-3,6-dimethoxy-2-isopropyl-5-(2'-iodo-4'-methoxybenzyl)-(2R,5S)-pyrazine (21)

The diastereomeric product 21 was obtained by a reaction of the lithium salt of the chiral auxiliary (2R)-2,5-dihydro-3,6-dimethoxy-2-isopropylpyrazine with the bromo derivative 20 using a crucial modification of a procedure reported in the literature [U. Schollkopf, "Enantioselective Synthesis of Non-Proteinogenic Amino Acids via Metallated Bis-Lactim Ethers of 2,5-Diketopiperazines." *Tetrahedron*, 39, pp 2085-2091 (1983)]. Briefly, (2R)-2,5-dihydro-3,6-dimethoxy-2-isopropylpyrazine (4.39 mL, 24.5 mmol) was dissolved in 4 mL of THF (freshly distilled from LiAlH₄). The light yellow solution was cooled to −78° C. (dry ice/acetone bath) and stirred for 15 min under argon. A 2.5 M solution of n-butyl lithium (9.79 mL, 24.5 mmol) was added drop wise over a period of 10 min and the mixture was stirred for 20 min at −78° C. In a separate flask CuCN (1.096 g, 12.23 mmol) was stirred with 4 mL of freshly distilled THF at room temperature for 10 min. The white suspension was then cooled to 0° C. (ice bath) and stirred at that temperature for 20 min. The n-BuLi reaction mixture was then transferred to the white suspension of CuCN/THF under argon using a cannula. The resulting yellow suspension turned into a yellow solution within two minutes. The reaction mixture was then stirred at 0° C. for 15 min and cooled to −78° C. After 15 min of stirring at −78° C., a solution of bromomethyl anisole derivative 20 (4.00 g, 12.23 mmol) in 6 mL of freshly distilled THF was added drop wise. The color of the reaction mixture changed to greenish brown. After stirring for a further period of 2 hours at −78° C., the reaction mixture was warmed gradually to room temperature. The reaction mixture was then poured into a saturated solution of NH₄Cl and extracted with EtOAc. The organic phase was dried over anhydrous Na₂SO₄, filtered and evaporated to provide an oily compound which was purified by flash column chromatography to yield pure 2,5-Dihydro-3,6-dimethoxy-2-isopropyl-5-(2-iodo-4-methoxybenzyl)-(2R,5S)-pyrazine (21) as a yellow oil (3.95 g, 75%).

¹H NMR (CDCl₃): δ 7.34 (d, 1H, H-3'), 7.1 (d, 1H, H-6'), 6.80 (dd, 1H, H-5'), 4.25 (dd, 1H, H-5), 3.75 (s, 3H, 4'-OMe), 3.73 (s, 3H, 6-OMe), 3.70 (d, 1H, H-2), 3.60 (s, 3H, 3-OCH₃), 3.60, 2.95 (dd, 2H, CH$_2$), 2.20 (m, 1H, CH of isopropyl), 1.00 (d, 3H, CH$_3$), 0.60 (d, 3H, CH$_3$).

$^{13}$C NMR (CDCl$_3$): δ 163.72 (C-3), 163.10 (C-6), 158.23 (C-4'), 133.22 (C-1'), 130.84 (C-6'), 124.23 (C-3'), 114.00 (C-5'), 101.50 (C-2'), 60.47 (C-2), 56.30 (C-5), 55.38 (4'-OCH$_3$), 52.54 (6-OCH$_3$), 52.39 (3-OMe), 43.63 (CH$_2$), 31.40 (CH of isopropyl), 19.06 (CH$_3$), 16.55 (CH$_3$).

MS (ESI) Calcd for C$_{17}$H$_{23}$IN$_2$O$_3$ (M$^+$): 430.08. Found: 431.07 (M$^+$+1).

Figure 15:
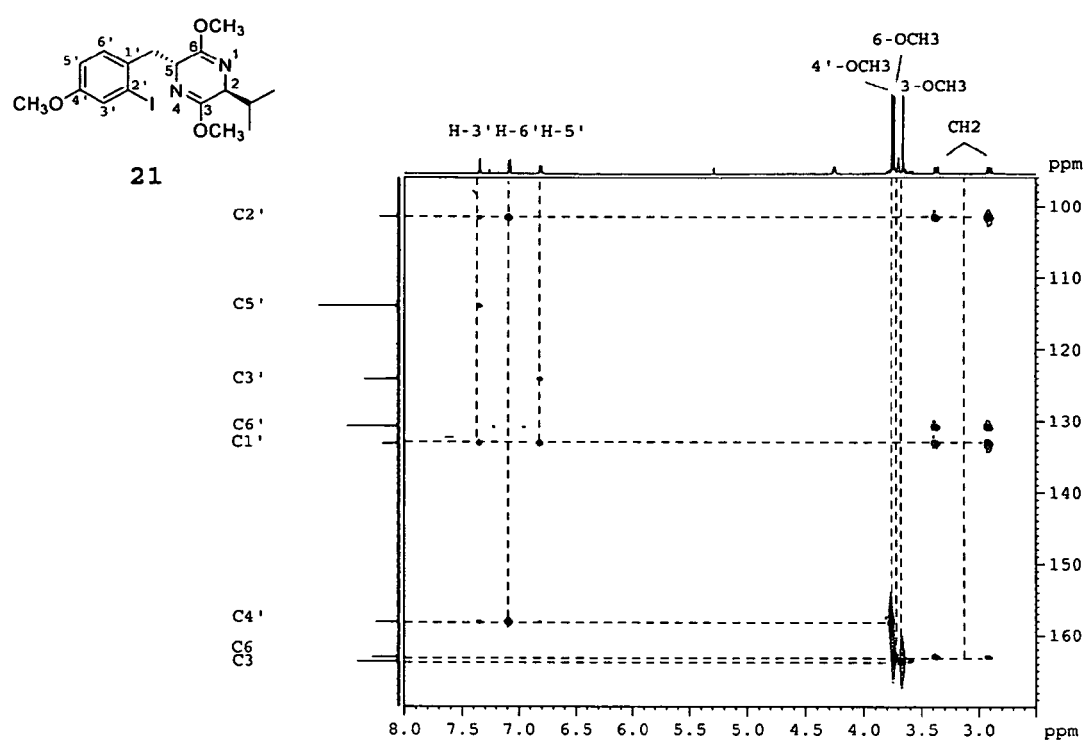
FIG. 15 shows 2,5-dihydro-3,6-dimethoxy-2-isopropyl-5-(2'-iodo-4'-methoxybenzyl)-(2R,5S)-pyrazine (21) and the C-13/H-1 HMBC NMR spectrum of this compound.

FIG. 15 shows the C-13/H-1 HMBC NMR spectrum of compound 21.

c) 2,5-Dihydro-3,6-dimethoxy-2-isopropyl-5-(2'-iodo-4'-methoxy-5'-formylbenzyl)-(2R,5S)-pyrazine (22)

Formylation of compound 21 by dichloromethyl methyl ether in the presence of stannic chloride was carried out by a known method [(A. H. Lewin, S. R. Parker, N. B. Fleming, and F. Carroll, "Formylation of Arenes by α,α-Dichloromethyl Methyl Ether. An Improved Experimental Procedure" *Org. Prep. Proced. Int.*, 10, pp 201-204 (1978)]. The pyrazine derivative 21 (100 mg, 0.23 mol) was dissolved in anhydrous dichloromethane (10 mL) and cooled to 0° C. and a 1M solution of SnCl$_4$ (2.6 mL, 2.6 mol) was added drop wise under argon. After completion of the addition of SnCl$_4$, 1,1-dichloromethyl methyl ether (0.21 mL, 2.32 mmol) was added drop wise to the reaction mixture. The solution turned from light yellow to greenish brown upon the addition of the dichloro derivative. The resulting mixture was stirred for 45 min at 0° C. A saturated solution of ammonium chloride (2 mL) was added to quench the reaction and the light brown suspension that resulted was stirred for 30 min at room temperature. The mixture was then extracted with dichloromethane. The organic phase was dried over anhydrous Na$_2$SO$_4$, filtered and evaporated, resulting in an oily product. Flash chromatographic purification of this product provided pure 2,5-dihydro-3,6-dimethoxy-2-isopropyl-5-(2'-iodo-4'-methoxy-5'-formylbenzyl)-(2R,5S)-pyrazine (22) as a yellow oil (51 mg, 48%).

$^1$H NMR (CDCl$_3$): δ 10.40 (s, 1H, CHO), 7.60 (s, 1H, H-6'), 7.40 (s, 1H, H-3'), 4.20 (dd, 1H, H-5), 3.85 (s, 3H, 4'-OCH$_3$), 3.65 (s, 4H, 6-CH$_3$, H-2), 3.60 (s, 3H, 3-OCH$_3$), 3.50, 2.90 (dd, 2H, CH$_2$), 2.20 (m, 1H, CH of isopropyl), 1.00 (d, 3H, CH$_3$), 0.60 (d, 3H, CH$_3$).

$^{13}$C NMR (CDCl$_3$): δ 189.17 (CHO), 163.86 (C-3), 162.67 (C-6), 159.35 (C-4'), 133.96 (C-1'), 129.87 (C-6'), 124.12 (C-5'), 122.73 (C-3'), 110.14 (C-2'), 60.56 (C-2), 55.90 (4'-OCH$_3$), 55.77 (C-5), 52.57 (3-OCH$_3$), 52.48 (6-OMe), 43.69 (CH$_2$), 31.51 (CH of isopropyl), 19.00 (CH$_3$), 16.53 (CH$_3$).

MS (ESI) Calcd for C$_{18}$H$_{23}$IN$_2$O$_4$ (M$^+$): 458.07. Found: 459.10 (M$^+$+1).

Figure 16:
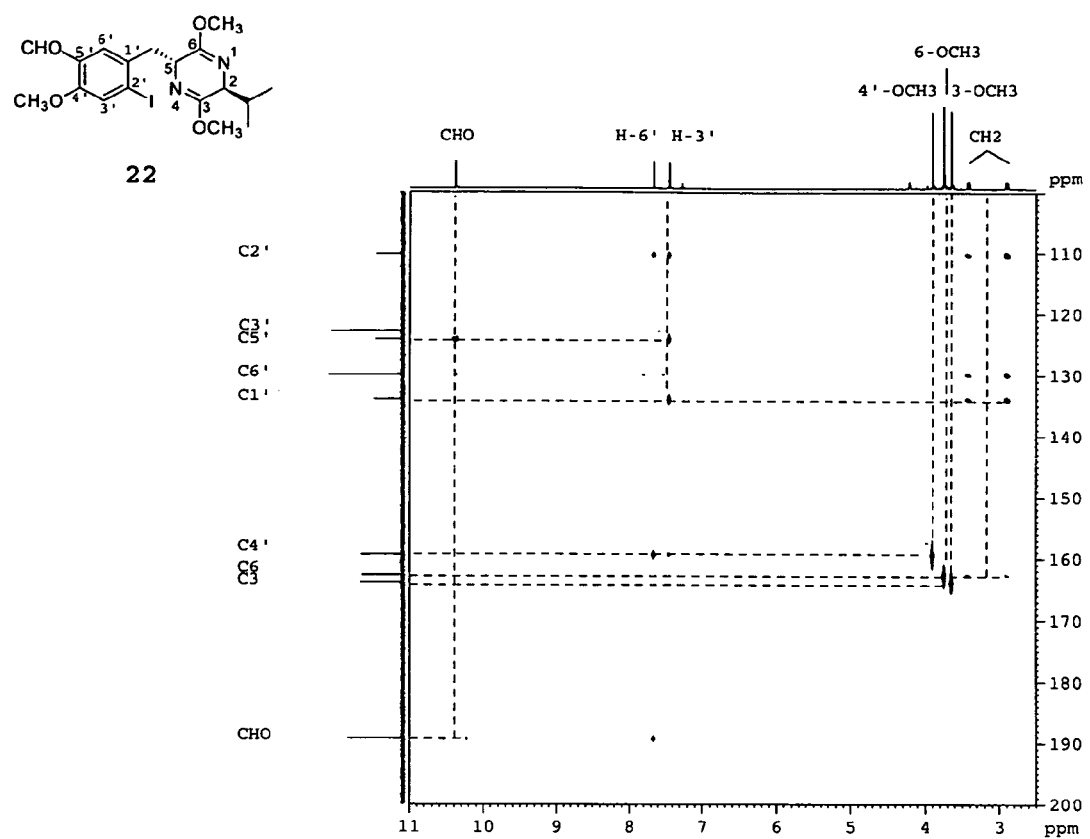
FIG. 16 shows 2,5-dihydro-3,6-dimethoxy-2-isopropyl-5-(2'-iodo-4'-methoxy-5'-formylbenzyl)-(2R,5S)-pyrazine (22) and the C-13/H-1 HMBC NMR spectrum of this compound.

FIG. 16 shows the C-13/H-1 HMBC NMR spectrum of 2,5-dihydro-3,6-dimethoxy-2-isopropyl-5-(2'-iodo-4'-methoxy-5'-formylbenzyl)-(2R,5S)-pyrazine (22).

d) 2,5-Dihydro-3,6-dimethoxy-2-isopropyl-5-(2'-iodyl-4'-methoxy-5'-formylbenzyl)-(2R,5S)-pyrazine (23)

A solution of the iodobenzyl pyrazine analog 22 (123.3 mg, 0.26 mmol) in anhydrous acetone (12 mL) was cooled in an ice bath and a freshly prepared solution of dimethyldioxirane (27 mL) was added drop wise. The solution was stirred for 2 hours at 0° C. The solvent was then evaporated to dryness to provide 2,5-dihydro-3,6-dimethoxy-2-isopropyl-5-(2'-iodyl-4'-methoxy-5'-formylbenzyl)-(2R,5S)-pyrazine (23) as a white solid in quantitative yield.

$^1$H NMR (DMSO-d$_6$): δ 10.36 (s, 1H, CHO), 7.70 (d, 2H, H-3', H-6'), 4.36 (dd, 1H, H-5), 3.99 (s, 3H, 4'-OCH$_3$), 3.68 (d, 6H, 3-OCH$_3$, 6-OCH$_3$), 3.60, 2.95 (dd, 2H, CH$_2$), 3.20 (d, 1H, H-2), 2.20 (m, 1H, CH of isopropyl), 0.94 (d, 3H, CH$_3$), 0.60 (d, 3H, CH$_3$).

MS (ESI) Calcd for C$_{18}$H$_{23}$IN$_2$O$_6$ (M+): 490.06. Found: 491.07 (M$^+$+1).

e) 2,5-Dihydro-3,6-dimethoxy-2-isopropyl-5-(2'-iodo-4'-hydroxy-5'-formylbenzyl)-(2R,5S)-pyrazine (24)

A 1M solution of BCl$_3$ in dichloromethane (11.8 mL, 11.8 mmol) was added drop wise to a solution of the methoxybenzyl pyrazine analog 22 (134.80 mg, 0.30 mmol) and stirred at 0° C. under argon. The solution changed in color from the initial orange to light brown and finally to greenish brown. The reaction mixture was stirred for one hour at 0° C. and warmed slowly to room temperature over night. The reaction mixture was poured into ice-water and stirred for 15 min. The mixture was extracted with dichloromethane and the organic phase was dried with Na$_2$SO$_4$. Evaporation of the solvent gave a yellow brown oil which upon flash chromatographic purification provided pure 2,5-dihydro-3,6-dimethoxy-2-isopropyl-5-(2'-iodo-4'-hydroxy-5'-formylbenzyl)-(2R,5S)-pyrazine (24) (41.40 mg, 32%).

$^1$H NMR (CDCl$_3$): δ 10.75 (s, 1H, OH), 9.80 (s, 1H, CHO), 7.60 (s, 1H, H-3'), 7.40 (s, 1H, H-6'), 4.20 (dd, 1H, H-5), 3.80 (t, 1H, H-2), 3.75 (s, 3H, 6-OCH$_3$), 3.60 (s, 3H, 3-OCH$_3$), 3.50, 2.90 (dd, 2H, CH$_2$), 2.20 (m, 1H, CH of isopropyl), 1.05 (d, 3H, CH$_3$), 0.70 (d, 3H, CH$_3$).

$^{13}$C NMR (CDCl$_3$): δ 196.05 (CHO), 164.02 (C-3), 162.74 (C-6), 158.92 (C-4'), 134.14 (C-6'), 133.16 (C-1'), 128.56 (C-3'), 120.36 (C-5'), 112.52 (C-2'), 60.72 (C-2), 55.93 (C-5), 52.53 (6-OCH$_3$), 52.51 (3-OCH$_3$), 43.50 (CH$_2$), 31.65 (CH of the isopropyl), 19.03 (CH$_3$), 16.62 (CH$_3$).

MS (ESI) Calcd for C$_{17}$H$_{21}$IN$_2$O$_4$ (M+): 444.05. Found: 445.07 (M$^+$+1).

Figure 17:
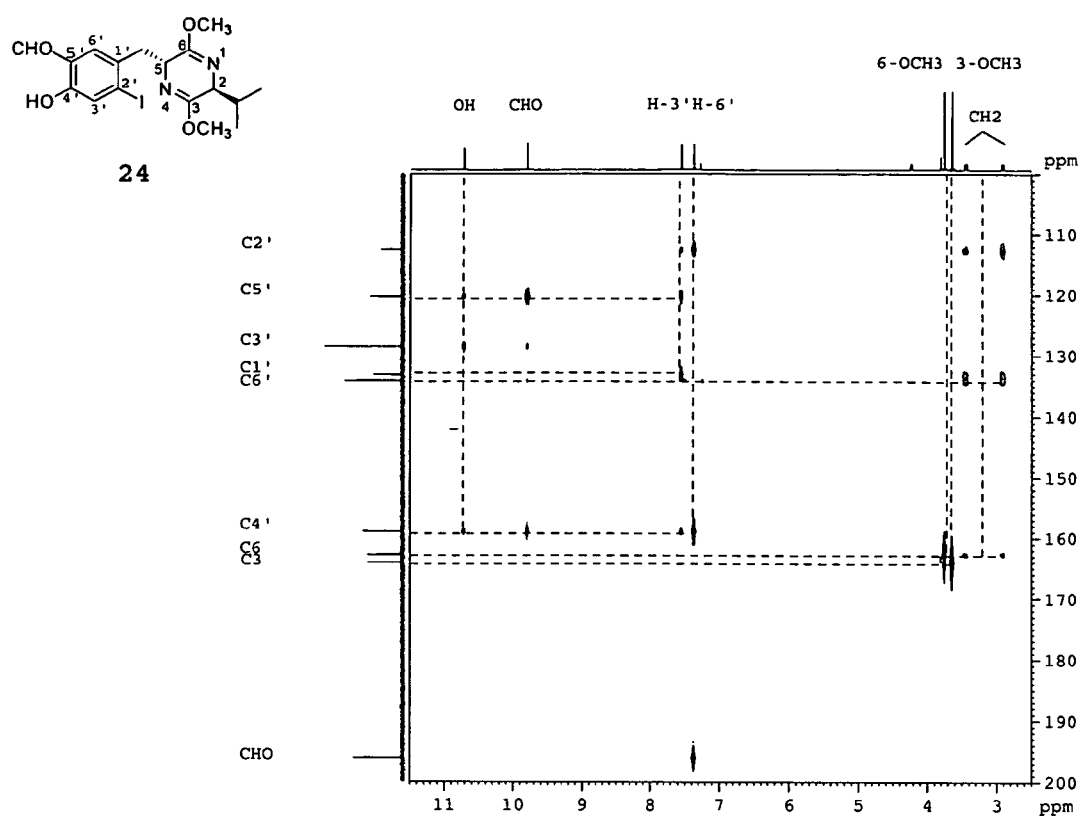
FIG. 17 shows 2,5-dihydro-3,6-dimethoxy-2-isopropyl-5-(2'-iodo-4'-hydroxy-5'-formylbenzyl)-(2R,5S)-pyrazine (24) and the C-13/H-1 HMBC NMR spectrum of this compound.

FIG. 17 shows the C-13/H-1 HMBC NMR spectrum for compound 24.

The phenolic group in the pyrazine derivative 24 upon reaction with (Boc)$_2$O in dimethylformamide led to the Boc protected analog 25 [$^1$H NMR (CDCl$_3$): δ 9.80 (s, 1H, CHO), 7.60 (s, 1H, H-3'), 7.40 (s, 1H, H-6'), 4.20 (dd, 1H, H-5), 3.80 (t, 1H, H-2), 3.75 (s, 3H, 6-OMe), 3.60 (s, 3H, 3-OMe), 3.50, 2.90 (dd, 2H, CH$_2$), 2.20 (m, 1H, CH of isopropyl), 1.60 (s, 9H, Boc-H), 1.05 (d, 3H, CH$_3$), 0.70 (d, 3H, CH$_3$)] which subsequently can be converted into the iodyl precursor 26 using the dimethyldioxirane reaction described above.

Example 18

The details of the synthesis of a third iodyl precursor for 6-[F-18]fluoro-L-dopa, shown in FIG. 18, is as follows:

a) (2S,5S)-tert-Butyl-5-(2'-iodo-4'-methoxybenzyl)-2-tert-butyl-3-methyl-4-oxoimidazolidine-1-carboxylate (27)

This product was obtained using the general procedure reported in the literature [(D. Seebach, E. Dziadulewicz, L. Behrendt, S. Cantoreggi, R. Fitzi, "Synthesis of Nonproteinogenic (R)- or (S)-Amino Acids Analogues of Phenylalanine, Isotopically Labelled and Cyclic Amino Acids from tert-Butyl 2-(tert-Butyl)-3-methyl-4-oxo-1-imidazolidinecarboxylate (Boc-BMI)." *Liebigs Ann. Chem.*, pp 1215-1232 (1989)]. Diisopropylamine (0.9 mL, 6.4 mmol) dissolved in dry THF (5 mL) was cooled to −78° C. under argon and a solution of BuLi (2.5 M in hexane, 2.5 mL) was added drop wise. After 20 min of stirring at −78° C., a solution of (S)-tert-butyl-2-tert-butyl-3-methyl-4-oxoimidazolidine-1-carboxylate (3.0 g, 11.9 mmol) was added drop wise and the reaction mixture was stirred for 30 min at −40° C. A solution of 2-iodo-4-methoxybenzyl bromide (20) (2.08 g, 6.4 mmol) in dry THF (2 mL) was then added drop wise to the reaction mixture. The new reaction mixture was stirred for 2 hours at the same temperature and then poured into a saturated solution of $NH_4Cl$. The product was extracted with EtOAc and the organic layer was washed with $NaHCO_3$ solution followed by brine. The organic phase was dried over anhydrous $Na_2SO_4$, filtered and evaporated to produce a yellow oil. Flash chromatographic purification of the oily product provided pure (2S,5S)-tert-Butyl-5-(2'-iodo-4'-methoxybenzyl)-2-tert-butyl-3-methyl-4-oxoimida-zolidine-1-carboxylate (27) as a white solid (743.7 mg, 23%).

$^1$H NMR ($CDCl_3$): δ 7.40 (s, 1H, H-3'), 6.80 (d, 2H, H-5', 6'), 5.09 (s, 1H, H-2), 4.36 (dd, 1H, H-5), 3.75 (s, 3H, 4'-$OCH_3$), 3.54, 3.40 (dd, 2H, $CH_2$), 3.03 (s, 3H, $NCH_3$), 1.33 (s, 9H, NBoc $CH_3$), 1.01 (s, 9H, tert-butyl $CH_3$).

$^{13}$C NMR ($CDCl_3$): δ 171.44 (C-4), 157.97 (C-4'), 131.66 (C-1'), 127.65 (C-6'), 124.92 (C-3'), 113.97 (C-5'), 101.78 (C-2'), 81.16 (Boc tert-C), 80.81 (C-5), 58.52 (C-2), 55.45 (4'-$OCH_3$), 40.74 (tert-butyl tert-C), 31.98 (C-7), 28.08 (Boc-$CH_3$, NMe), 26.40 (tert-butyl $CH_3$).

MS (ESI) Calcd for $C_{21}H_{31}IN_2O_4$ ($M^+$): 502.13. Found: 503.13 ($M^+$+1).

Figure 19:
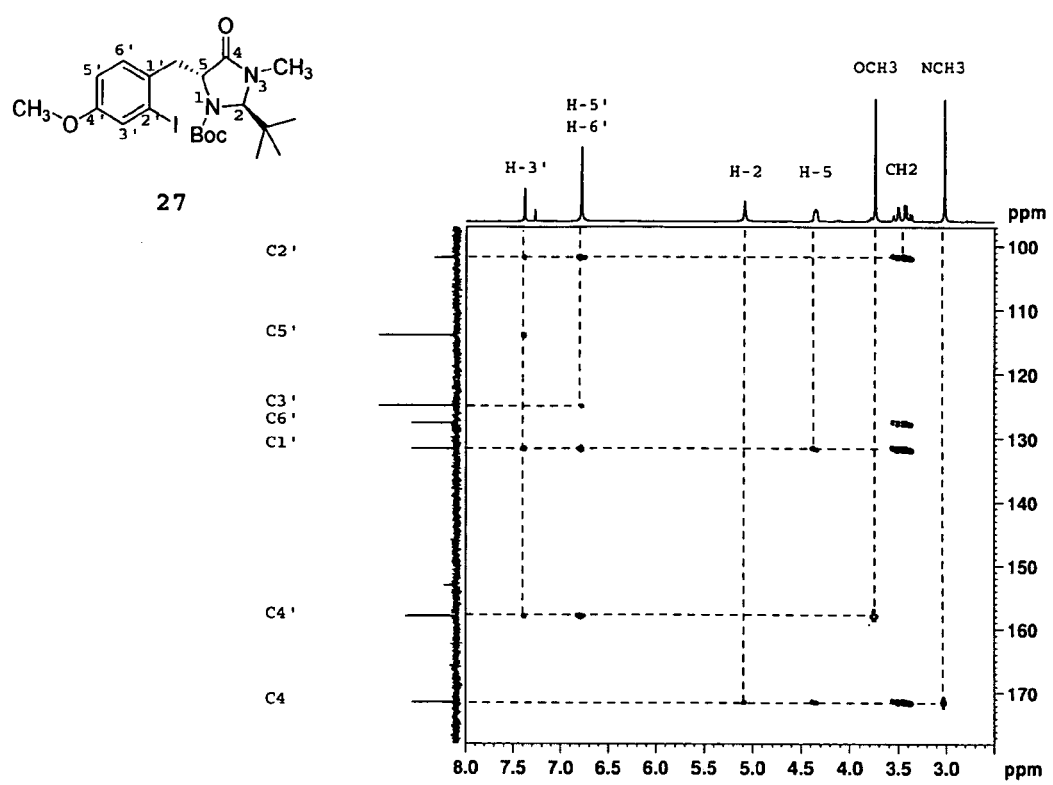
FIG. 19 shows the C-13/H-1 HMBC NMR spectrum of a key intermediate, namely (2S,5S)-tert-butyl-5-(2'-iodo-4'-methoxybenzyl)-2-tert-butyl-3-methyl-4-oxoimidazolidine-1-carboxylate (27).

FIG. 19 shows the C-13/H-1 HMBC NMR spectrum of compound 27.

b) (2S,5S)-tert-Butyl-5-(2'-iodo-4'-methoxy-5'-formylbenzyl)-2-tert-butyl-3-methyl-4-oxoimidazolidine-1-carboxylate (28)

The iodoanisole derivative 27 (460.20 mg, 0.94 mmol) was dissolved in anhydrous dichloromethane (10 mL) and cooled to 0° C. under argon. After stirring for 15 min a solution of $SnCl_4$ (1M in dichloromethane, 10.4 mL, 10.4 mmol) was added drop wise. After completion of the addition of $SnCl_4$, 1,1-dichloromethyl methyl ether (0.84 mL, 9.4 mmol) was added drop wise. The color of the solution turned from light yellow to greenish brown. The reaction mixture was stirred for 45 min at 0° C. and then quenched with a saturated solution of ammonium chloride (2.0 mL). The light brown suspension was stirred for 30 min at room temperature and extracted with dichloromethane. The organic phase was dried over anhydrous $Na_2SO_4$, filtered and evaporated to afford a yellow oil. Flash chromatographic purification of the crude product gave pure (2S,5S)-tert-Butyl-5-(2'-iodo-4'-methoxy-5'-formylbenzyl)-2-tert-butyl-3-methyl-4-oxoimidazolidine-1-carboxylate (28) as oil (57 mg, 10%).

$^1$H NMR ($CDCl_3$): δ 10.40 (s, 1H, CHO), 7.52 (s, 1H, H-3'), 7.32 (s, 1H, H-6'), 5.25 (s, 1H, H-2), 4.52 (dd, 1H, H-5), 3.92 (s, 3H, 4'-$OCH_3$), 3.87, 2.98 (dd, 2H, $CH_2$), 3.89 (s, 3H, $NCH_3$), 1.6 (s, 9H, NBoc $CH_3$), 1.1 (s, 9H, tert-butyl $CH_3$).

Dimethyldioxirane mediated oxidation of (2S,5S)-tert-Butyl-5-(2'-iodo-4'-methoxy-5'-formylbenzyl)-2-tert-butyl-3-methyl-4-oxoimidazolidine-1-carboxylate (28) results in the iodyl precursor 29.

Example 19

Figure 20:
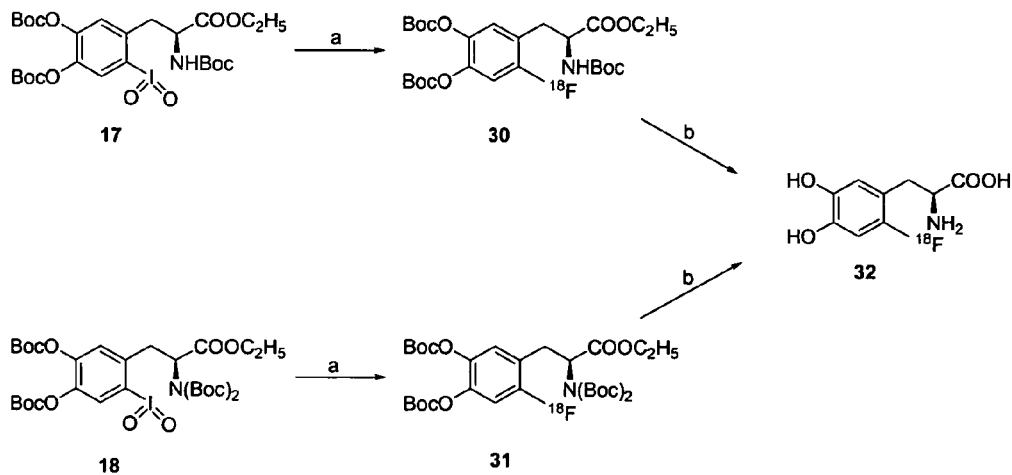
FIG. 20 shows the reaction scheme for the synthesis of 6-[F-18]fluoro-L-dopa (32) from N-(tert-butoxycarbonyl)-3,4-di(tert-butoxycarbonyloxy)-6-iodyl-L-phenylalanine ethyl ester (17) and N-di-(tert-butoxycarbonyl)-3,4-di(tert-butoxycarbonyloxy)-6-iodyl-L-phenylalanine ethyl ester (18).

The iodyl precursors 17 and 18 when reacted with dry no-carrier-added [F-18] KF/Kryptofix or [F-18] quaternary ammonium fluoride salts (e.g. n-$Bu_4NF$, $(PhCH_2)_4NF$) (in dry DMSO medium; 140° C. for 15-30 min) gave the corresponding F-18 labeled intermediates 30 and 31, respectively in 5-10% radiochemical yields (corrected for F-18 decay) (FIG. 20). The intermediates were isolated using a C-18 Sep-Pak as described earlier. Hydrolysis of these intermediates by mineral acids as set forth in M. Namavari, A. Bishop, N. Satyamurthy, G. Bida and J. R. Barrio, "Regioselective Radiofluorodestannylation with [$^{18}$F]$F_2$ and [$^{18}$F]$CH_3COOF$: A High Yield Synthesis of 6-[$^{18}$F]Fluoro-L-Dopa." *Appl. Radiat. Isot.*, 43, pp 989-996 (1992) would lead to 6-[F-18]fluoro-L-dopa (32).

Example 20

Figure 21:
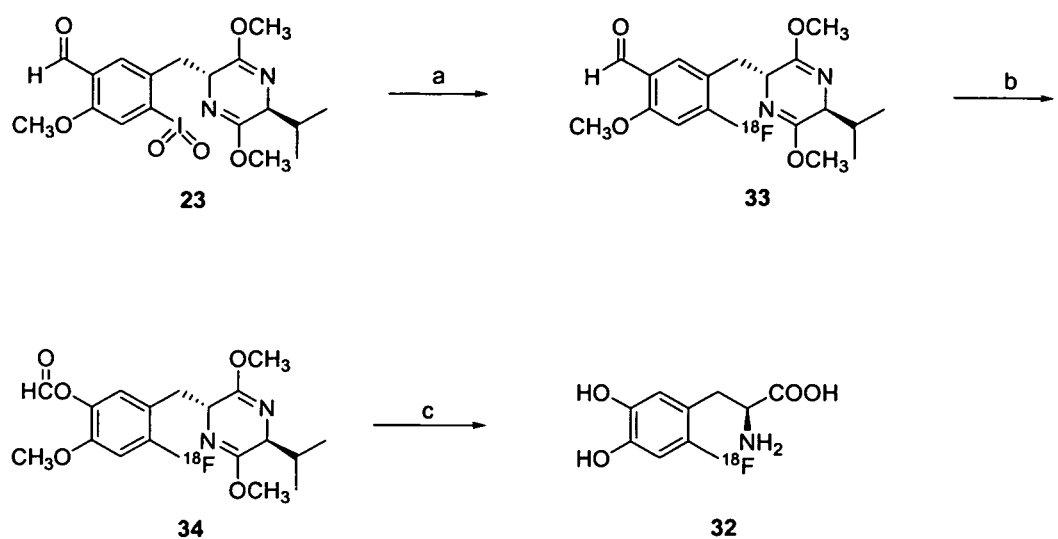
FIG. 21 shows the reaction scheme used for the synthesis of 6-[F-18]fluoro-L-dopa (32) from 2,5-dihydro-3,6-dimethoxy-2-isopropyl-5-(2'-iodyl-4'-methoxy-5'-formylbenzyl)-(2R,5S)-pyrazine (23).

A second and more efficient synthetic scheme for the preparation of 6-[F-18]fluoro-L-dopa (32), shown in FIG. 21, is as follows:

a) 2,5-Dihydro-3,6-dimethoxy-2-isopropyl-5-(2'[F-18]fluoro-4'-methoxy-5'-formylbenzyl)-(2R,5S)-pyrazine (33)

Figure 22:
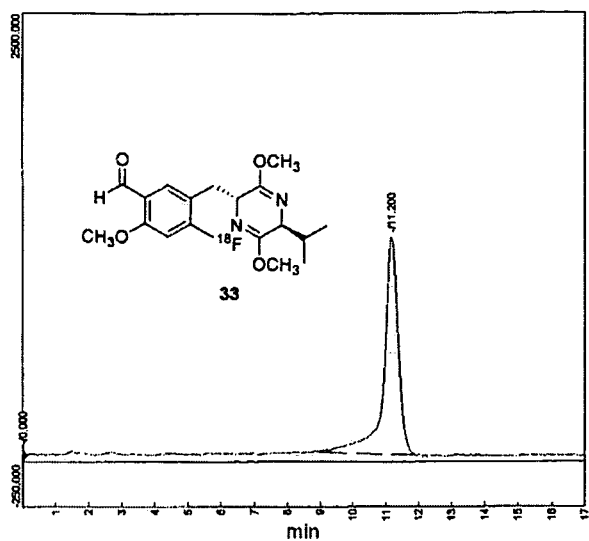
FIG. 22 shows the test conditions and the analytical radio HPLC trace of the crude radiofluorination product 2,5-dihydro-3,6-dimethoxy-2-isopropyl-5-(2'-[F-18]fluoro-4'-methoxy-5'-formylbenzyl)-(2R,5S)-pyrazine (33) obtained from the reaction of 2,5-dihydro-3,6-dimethoxy-2-isopropyl-5-(2'-iodyl-4'-methoxy-5'-formylbenzyl)-(2R,5S)-pyrazine (23) with no-carrier-added [F-18]fluoride ion.
Figure 23:
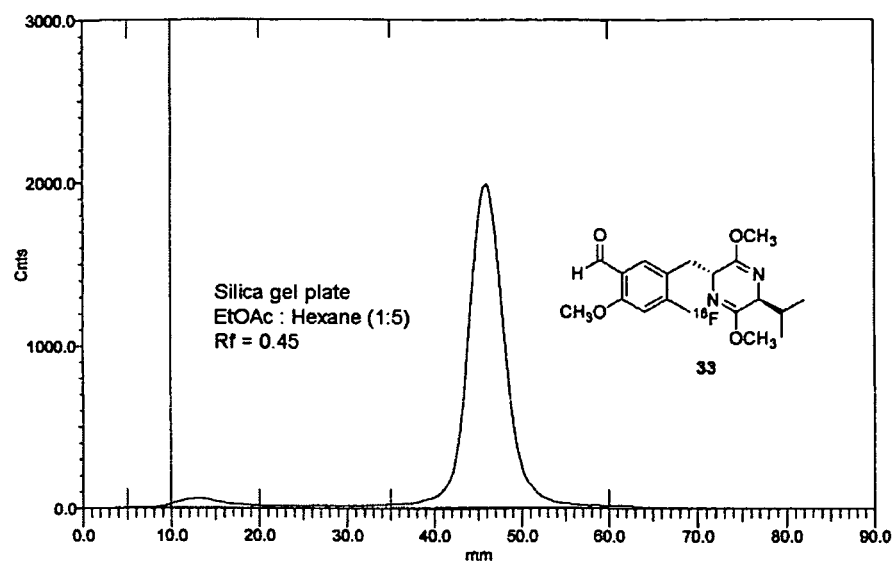
FIG. 23 shows the radio TLC trace of the crude radiofluorination product 2,5-dihydro-3,6-dimethoxy-2-isopropyl-5-(2'[F-18]fluoro-4'-methoxy-5'-formylbenzyl)-(2R,5S)-pyrazine (33) obtained from the reaction of 2,5-dihydro-3,6-dimethoxy-2-isopropyl-5-(2'-iodyl-4'-methoxy-5'-formylbenzyl)-(2R,5S)-pyrazine (23) with no-carrier-added [F-18]fluoride ion.

No-carrier-added [F-18]fluoride ion was produced by proton bombardment of [O-18]water in a cyclotron target body. The aqueous [F-18]fluoride ion was treated with 1.0 mg of potassium carbonate and 10 mg of Kryptofix 2.2.2.®, the solution was evaporated at 100-120° C. and the residue was further dried by azeotropic distillation with acetonitrile to provide [F-18]KF/Kryptofix® complex. Alternatively, dry no-carrier-added quaternary ammonium [F-18]fluorides (e.g. $Me_4NF$, $Et_4NF$, n-$Bu_4NF$, $(PhCH_2)_4NF$) were prepared from the corresponding bicarbonate salts (1.0 mg each). Evaporation of water and the subsequent azeotropic drying of the residue with acetonitrile, in the case of the [F-18] quaternary ammonium fluorides, were conducted at 80° C. under vacuum. The benzyliodyl pyrazine derivative 23 (5 mg) was dissolved in dry DMSO (1 mL) and added to the dried no-carrier-added potassium [F-18]fluoride/Kryptofix complex or a [F-18] quaternary ammonium fluoride. The reaction vessel was then hermetically sealed with a glass or silicone stopper and heated at 150° C. for 10 min. The reaction mixture was cooled to room temperature and diluted with water (10 mL) and passed through a C-18 Sep-Pak® column pre-equilibrated with methanol (5 mL) followed by water (10 mL). The Sep-Pak® column was flushed with 10 mL of water and the product, 2,5-dihydro-3,6-dimethoxy-2-isopropyl-5-(2'-[F-18]-4'-methoxy-5'-formylbenzyl)-(2R,5S)-pyrazine (33) was eluted off with 2 mL of acetonitrile in 70% radiochemical yield (corrected for F-18 decay). The F-18 labeled product was found to ≥95% radiochemically pure as evidenced by radioHPLC and radioTLC analyses (FIGS. 22 and 23).

b) 2,5-Dihydro-3,6-dimethoxy-2-isopropyl-5-(2'[F-18]fluoro-4'-methoxybenzyl)-(2R,5S)-pyrazine-5'-formate (34)

Figure 24:
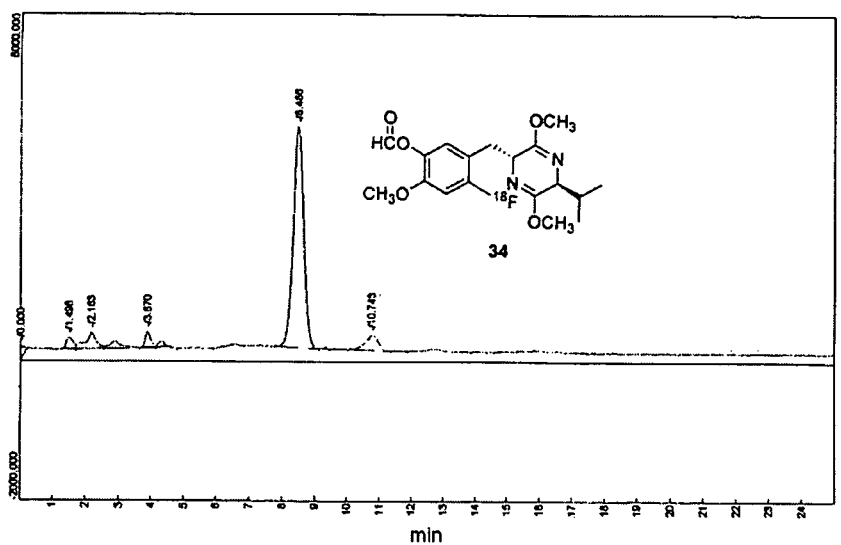
FIG. 24 shows the test conditions and the analytical radio HPLC trace of the crude product 2,5-dihydro-3,6-dimethoxy-2-isopropyl-5-(2'-[F-18]fluoro-4'-methoxybenzyl)-(2R,5S)-pyrazine-5'-formate (34) obtained by the Baeyer-Villiger oxidation reaction of 2,5-dihydro-3,6-dimethoxy-2-isopropyl-5-(2'-[F-18]-4'-methoxy-5'-formylbenzyl)-(2R,5S)-pyrazine (33).

Baeyer-Villiger oxidation of the F-18 labeled benzaldehyde analog 33 to give the corresponding formate ester 34 was carried out by a reported procedure [I. Ekaeva, L. Barre, M.-C. Lasne and F. Gourand, "2- and 4-[$^{18}$F]Fluorophenols from Baeyer-Villiger Oxidation of [$^{18}$F]Fluorophenylketones and [$^{18}$F]Fluorobenzaldehydes" *Appl. Radiat. Isot.*, 46, pp 777-782 (1995)]. In accordance with that procedure 2,5-dihydro-3,6-dimethoxy-2-isopropyl-5-(2'-[F-18]-4'-methoxy-5'-formylbenzyl)-(2R,5S)-pyrazine (33) obtained as above in acetonitrile was evaporated to dryness and a solution of 3-chloroperoxybenzoic acid (10 mg) in dichloromethane (1.0 mL) was added. The reaction vessel was hermetically sealed and heated at 70° C. for 20 min. The product 2,5-dihydro-3,6-dimethoxy-2-isopropyl-5-(2'-[F-18]fluoro-4'-methoxybenzyl)-(2R,5S)-pyrazine-5'-formate (34) formed in this reaction was utilized in the next step of the reaction without being isolated. However, an aliquot of the reaction mixture was analyzed by analytical HPLC and the efficiency of this reaction was found to be 75% (FIG. 24).

c) 6-[F-18]Fluoro-L-dopa (32)

Figure 25:
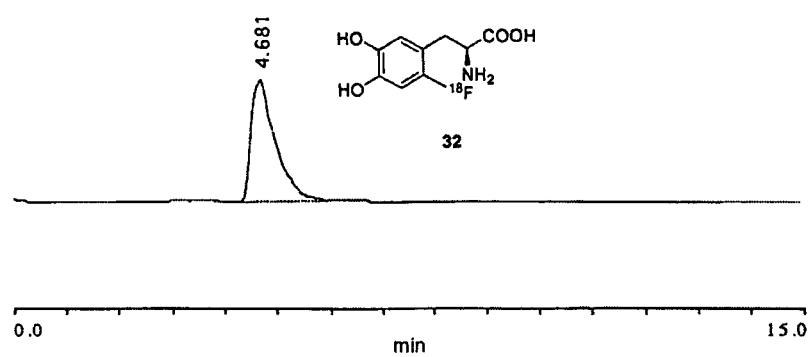
FIG. 25 shows the analytical radio HPLC trace of the semi-prep HPLC purified sample of 6-[F-18]fluoro-L-dopa (32) obtained using the reaction scheme depicted in FIG. 21.

2,5-Dihydro-3,6-dimethoxy-2-isopropyl-5-(2'-[F-18]fluoro-4'-methoxybenzyl)-(2R,5S)-pyrazine-5'-formate (34), obtained above in dichloromethane solution, was evaporated to dryness and 1 mL of 54% HI was added to residue. The reaction mixture was heated at 130° C. for 15-30 min. Alternatively, the hydrolysis can be effected by first heating with methanesulfonic acid (0.3 mL) followed 48% HBr (1 mL). The reaction mixture was cooled to room temperature and partially neutralized with 3M NaOH solution in water (0.75 mL) and then diluted with 1.3 mL of a mixture of 5 mM sodium acetate, 1 mM EDTA, 0.1% acetic acid and 0.01% ascorbic acid. The solution was injected onto an Alltech Adsorbosphere C-18 semiprep HPLC column and eluted with a mobile phase of 5 mM sodium acetate, 1 mM EDTA, 0.1% acetic acid and 0.01% ascorbic acid at a flow rate of 5.0 mL/min. The HPLC column effluent was monitored by a radioactivity detector. 6-[F-18]fluoro-L-dopa (32) that eluted off the column was collected and identified by analytical HPLC (FIG. 25). The above examples detail the procedure for preparation of specific compounds.

One skilled in the art will recognize, based on the teachings herein, that the process described herein, or similar processes can be used to prepare various different iodyl compounds. Therefore, it is to be understood that the inventions are not to be limited to the specific embodiments disclosed and that modifications and other embodiments are intended to be included within the scope of the appended claims. Described below are compounds, all of which are contemplated by the present invention.

Compound 35 shown below, for example, is derived from 4-methoxy-2-iodophenylalanine, a known compound reported in the literature [T. J. McCord, D. E. Thornton, K. L. Hulme and A. L. Davis, "Synthesis and Microbiological Properties of 2-Iodotyrosine and Related Compounds." *Texas J. Sci.*, 30, pp 357-363 (1978)]. It can be prepared as follows:

Compound 35

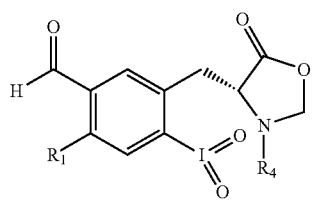

wherein:
$R_1$=H, $OCH_3$, $OCH_2Ph$, O-Boc, O-Methoxytrityl
$R_4$=$COCH_3$, $COCF_3$,
$CH_2Ph$, $COOCH_2Ph$,
Boc The amino group in 4-methoxy-2-iodophenylalanine is protected with $COCH_3$, $COCF_3$, $CH_2Ph$, $COOCH_2Ph$ or Boc by standard protection techniques and cyclized with the carboxy group by a reaction with formaldehyde as shown in the literature. These analogs upon treatment with dichloromethyl methyl ether in the presence of stannic chloride, as described in paragraph [0080], will yield the aldehyde derivatives which upon oxidation by DMDO, as described in paragraph [0081], will provide the iodyl precursor 35.

Compound 36

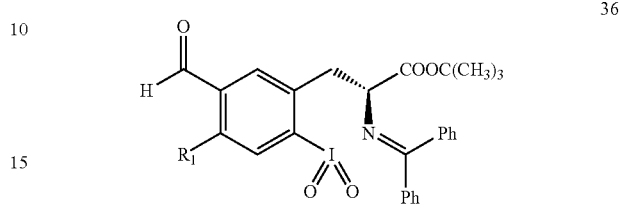

wherein:
$R_1$=H, $OCH_3$, $OCH_2Ph$, O-Boc, O-Methoxytrityl

The compound 20 (shown in FIG. 13) upon reaction with N-(diphenylmethylene) glycine tert-butylester as set forth in C. Lemaire, S. Gillet, S. Guillouet, A. Plenevaux, J. Aerts and A. Luxen, "Highly Enantioselective Synthesis of No-Carrier-added 6-[18F]Fluoro-L-Dopa by Chiral Phase-Transfer Alkylation." Eur. J. Org. Chem., pp 2899-2904 (2004) will provide a chiral amino acid derivative which can be formylated and then oxidized with DMDO, as described above, will provide the iodyl compound 36.

Compound 37

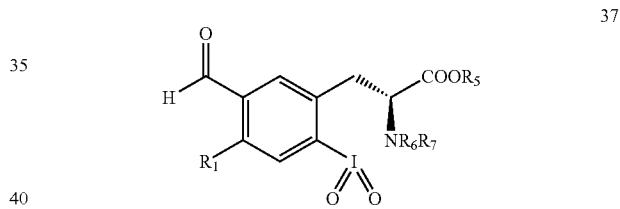

wherein:
$R_1$=H, $OCH_3$, $OCH_2Ph$, O-Boc, O-Methoxytrityl
$R_5$=$CH_3$, $C_2H_5$, $CH_2Ph$, $C(CH_3)_3$
$R_6$, $R_7$=H, $COCH_3$, $COCF_3$, $COOCH_2Ph$, Boc, $CH_2Ph$ The carboxyl group and the amino group in 4-methoxy-2-iodophenylalanine [T. J. McCord, D. E. Thornton, K. L. Hulme and A. L. Davis, "Synthesis and Microbiological Properties of 2-Iodotyrosine and Related Compounds." *Texas J. Sci.*, 30, pp 357-363 (1978)] are protected by the designated $R_5$, $R_6$ and $R_7$ groups by the standard techniques. The compound is then subjected to formylation and the oxidation of the iodo group by DMDO, as described above, to produce the iodyl compound 37.

Compound 38

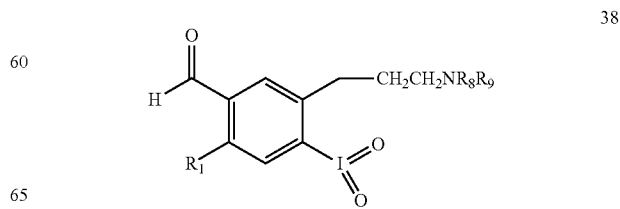

wherein:
R$_1$=H, OCH$_3$, OCH$_2$Ph, O-Boc, O-Methoxytrityl
R$_8$, R$_9$=H, COCH$_3$, COCF$_3$, CH$_2$Ph, COOCH$_2$Ph, Boc Compound 20 (shown in FIG. 13), upon reaction with sodium cyanide the bromo group will be replaced to provide the corresponding nitrile which, upon reduction with lithium aluminum hydride, will yield an amino analog. The amino function can then be protected with the R$_8$ and R$_9$ groups. The protected derivatives, upon formylation with dichloromethyl methyl ether followed by DMDO oxidation, as described above, will provide the iodyl compound 38.

Compound 39

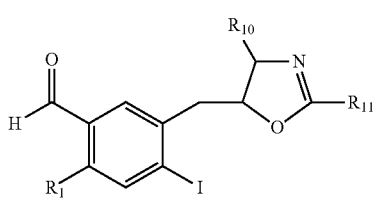

39 wherein:
R$_1$=H, OCH$_3$, OCH$_2$Ph, O-Boc, O-Methoxytrityl
R$_{10}$=H, CH$_3$
R$_{11}$=CH$_3$, Ph The derivative represented by the structure 39 can be prepared from compound 20 (shown in FIG. 13). The bromo compound 20 upon oxidation produces a benzaldehyde derivative. Reaction of the benzaldehyde derivative with nitroethane followed by reduction with Pd/C and then cyclization of the amino alcohol as set forth in N. F. Albertson, F. C. McKay, H. E. Lapf, J. O. Hoppe, W. H. Selberis and A. Arnold, "The Optical Isomers of Metaraminol. Synthesis and Biological Activities." J. Med. Chem., 13, pp 132-134 (1970) will yield a cyclized intermediate. The formylation of that intermediate followed by DMDO oxidation of the iodo moiety results in the iodyl compound 39.

Amino acids with D-configurations can be prepared using the methods described in FIGS. 13 and 18 by starting with the D-chiral precursors instead of the L-chiral precursors. The reaction conditions are identical for both D and L isomers. Nucleophilic [F-18] fluorination and Baeyer-Villiger oxidation followed by acid hydrolysis will provide the D-amino acids.

Current general methodology of aromatic nucleophilic radiofluorination reactions involves the displacement of a nitro, quaternary ammonium group or a positively charged iodonium moiety by [F-18] fluoride ion. Nitroaromatic compounds and the fluoro-products obtained from them have very similar chromatographic properties and thus their separation is frequently difficult to accomplish. On the other hand, the synthesis of quaternary ammonium group substituted complex aromatic compounds is extremely difficult. Similarly, the synthesis of iodonium salt based precursors of complex molecules is also difficult. Moreover, the reaction of iodonium salts with [F-18] fluoride ion generally provides two radiolabeled products, one of which is an unwanted one. It has been discovered that the use of the reaction scheme described herein using iodylbenzene derivatives as starting materials provides an easily accomplished, high yield reaction and the production of readily separated and purified fluorinated compounds. Nucleophilic aromatic substitution reactions such as described herein for the attachment of no-carrier-added [F-18] fluorine have not been described in the art. Because a large number of compounds used in PET diagnostic procedures have an aryfluoro moiety, the preparative procedures set forth herein will have a major impact on the ability to produce suitable F-18 labeled compounds for PET procedures as well as other diagnostic techniques designed to detect abnormal tissue and disease states within the body and particularly to brain disorders.

While the synthesis of [F-18] labeled compounds is described above, the reaction schemes set forth are not limited to the production of fluorine labeled compounds. Using the same techniques and reaction schemes, other nucleophiles, for example, chloride, bromide or iodide anions, can be used to label compounds of interest. These anions, or other suitable anions, available in forms which release radio-detectable emissions can be added to the compounds of interest using the general fluoride ion nucleophilic reaction schemes described above for the synthesis, for example, of arylchlorides, arylbromides or aryliodides. Examples of useful isotopes of chlorine are Cl-34m, and Cl-39, useful isotopes of bromine are Br-75, Br-76 and Br-77 and useful isotopes of iodine are I-123, I-124 and I-125.

We claim:

1. A procedure for preparing F-18 labeled compounds identified as product in the table below comprising:

providing a benzene derivative containing an iodyl group and an aqueous solution of [F-18] fluoride ion replacing the iodyl group by said F-18 ion to produce an F-18 containing benzene derivative, the F-18 ion being free of a fluoride ion carrier wherein the benzene derivative containing an iodyl group is selected from the group listed in the left hand column of the table below and the F-18 containing benzene derivative produced therefrom is listed in the corresponding right hand column of the table below:

| Benzene Derivative Containing Iodine | Product |
|---|---|
| IO$_2$–C$_6$H$_5$ | $^{18}$F–C$_6$H$_5$ |
| 4-IO$_2$–C$_6$H$_4$–CH$_3$ | 4-$^{18}$F–C$_6$H$_4$–CH$_3$ |
| 4-IO$_2$–C$_6$H$_4$–Cl | 4-$^{18}$F–C$_6$H$_4$–Cl |

-continued

| Benzene Derivative Containing Iodine | Product |
|---|---|

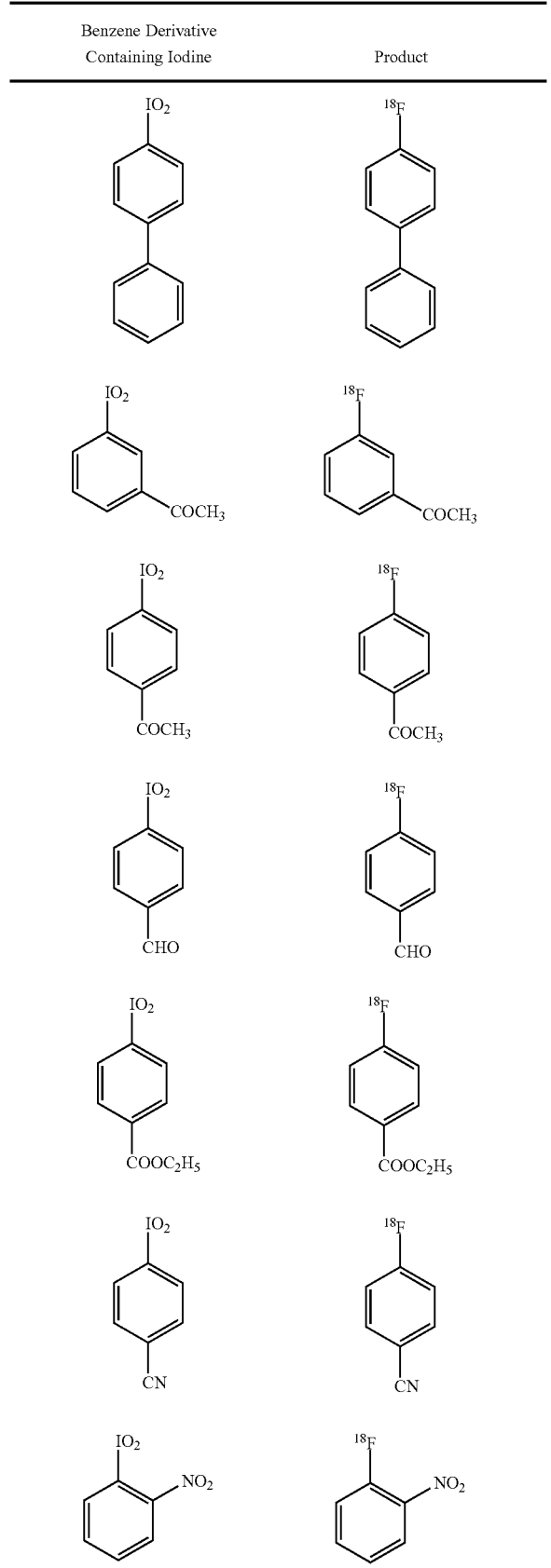
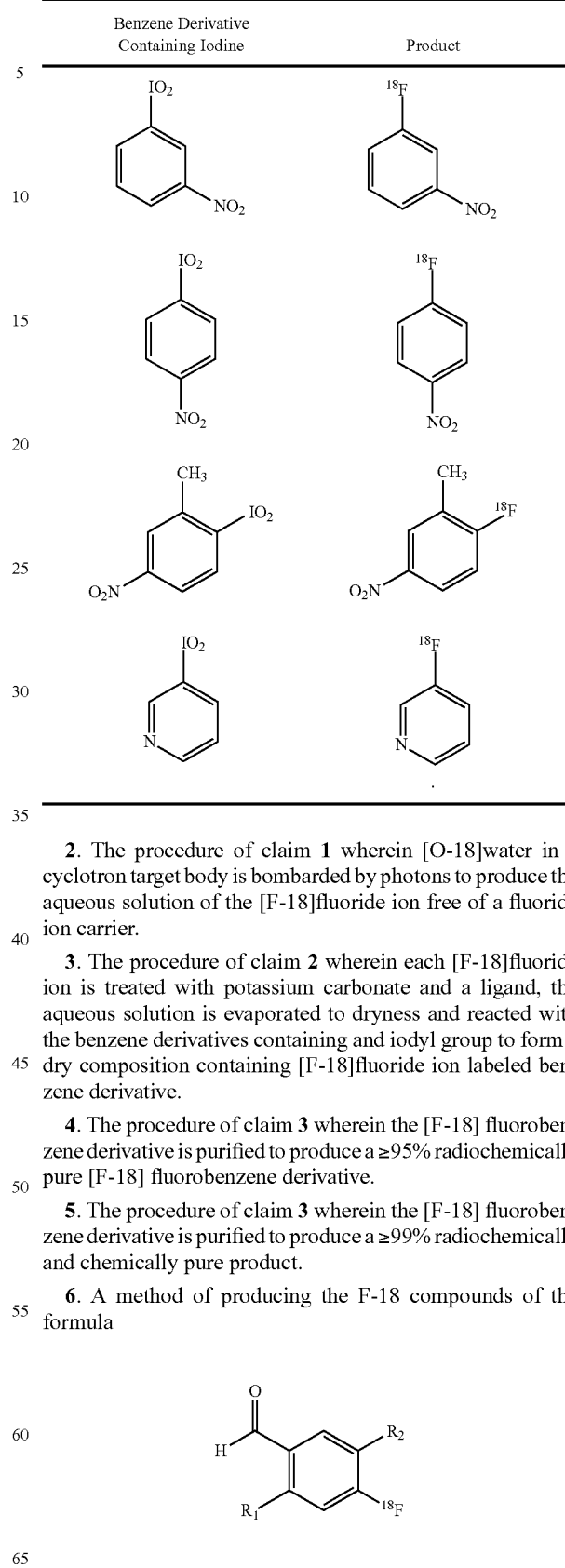

2. The procedure of claim 1 wherein [O-18]water in a cyclotron target body is bombarded by photons to produce the aqueous solution of the [F-18]fluoride ion free of a fluoride ion carrier.

3. The procedure of claim 2 wherein each [F-18]fluoride ion is treated with potassium carbonate and a ligand, the aqueous solution is evaporated to dryness and reacted with the benzene derivatives containing and iodyl group to form a dry composition containing [F-18]fluoride ion labeled benzene derivative.

4. The procedure of claim 3 wherein the [F-18] fluorobenzene derivative is purified to produce a ≥95% radiochemically pure [F-18] fluorobenzene derivative.

5. The procedure of claim 3 wherein the [F-18] fluorobenzene derivative is purified to produce a ≥99% radiochemically and chemically pure product.

6. A method of producing the F-18 compounds of the formula $$\text{structure with } H-C(=O)-\text{benzene ring with } R_1, R_2, \text{ and } ^{18}F \text{ substituents}$$

by subjecting an iodine containing compound of the formula

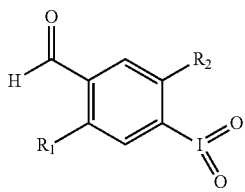

to dry/anhydrous no-carrier-added F-18 fluoride ion using conventional dry heating procedures or under microwave heating where the [F-18] fluoride ion is derived from [F-18]KF/Kryptofix complex, [F-18]CsF or [F-18] quaternary ammonium fluoride, the quaternary ammonium groups selected from tetramethyl, tetraethyl, tetra n-butyl, and tetrabenzyl
wherein:
$R_1$=H, $OCH_3$, $OCH_2Ph$, O-Boc, O-Methoxytrityl

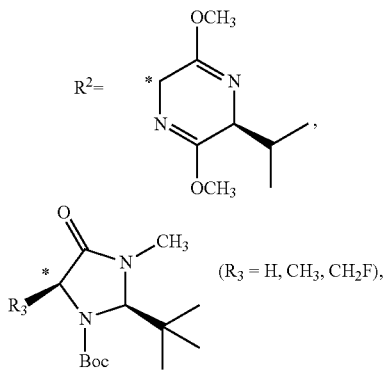

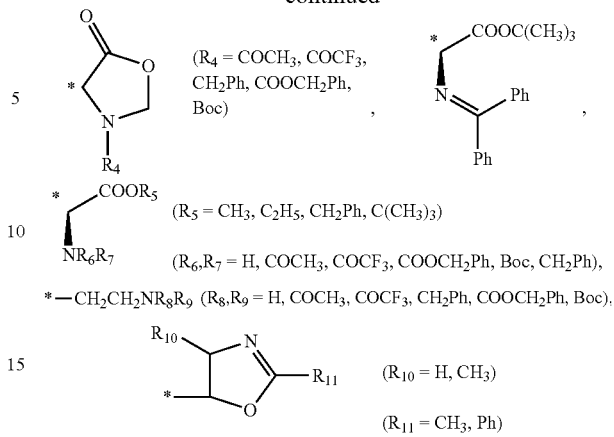

wherein $R_2$ is bonded to the iodine containing compound at a C atom identified by *.

7. The method of claim 6 wherein one or more ketone groups in the F-18 compounds are oxidized using the Baeyer-Villiger reaction to form one or more ester groups.

8. The method of claim 6 further comprising producing F-18 labeled amino acids, F-18 labeled amines or F-18 labeled amino alcohols by hydrolyzing the F-18 compounds using conventional dry heating or microwave heating with mineral acids or organic acids.

9. The method of claim 8 wherein the mineral acids comprise HCl, HBr or HI and the organic acids comprise methanesulfonic acid, or trifluoromethane sulfonic acid.

* * * * *